US009381299B2

(12) United States Patent
Kuo et al.

(10) Patent No.: US 9,381,299 B2
(45) Date of Patent: Jul. 5, 2016

(54) IMPLANTABLE DRUG DELIVERY DEVICES

(71) Applicants: Youti Kuo, Penfield, NY (US); Michael R. Violante, Pittsford, NY (US)

(72) Inventors: Youti Kuo, Penfield, NY (US); Michael R. Violante, Pittsford, NY (US)

(73) Assignee: Kuvio, Inc., Pittsford, NY (US)

( * ) Notice: Subject to any disclaimer, the term of this patent is extended or adjusted under 35 U.S.C. 154(b) by 87 days.

(21) Appl. No.: 14/093,915

(22) Filed: Dec. 2, 2013

(65) Prior Publication Data
US 2014/0142556 A1 May 22, 2014

Related U.S. Application Data

(62) Division of application No. 13/201,960, filed as application No. PCT/US2010/024430 on Feb. 17, 2010, now Pat. No. 8,603,051.

(60) Provisional application No. 61/207,587, filed on Feb. 17, 2009, provisional application No. 61/210,949, filed on Mar. 25, 2009, provisional application No. 61/211,784, filed on Apr. 3, 2009.

(51) Int. Cl.
*A61K 9/22* (2006.01)
*A61M 5/142* (2006.01)
(Continued)

(52) U.S. Cl.
CPC ............ *A61M 5/14276* (2013.01); *A61J 1/067* (2013.01); *A61J 1/14* (2013.01); *A61M 5/1407* (2013.01); *A61M 5/168* (2013.01); *A61M 5/14216* (2013.01); *A61M 39/0208* (2013.01); *A61M 2005/1402* (2013.01);
(Continued)

(58) Field of Classification Search
CPC ............ A61M 2005/14513; A61M 2209/045; A61M 5/1407; A61M 5/14276; A61M 5/168; A61J 1/067; A61J 1/14
See application file for complete search history.

(56) References Cited

U.S. PATENT DOCUMENTS 5,085,656 A   2/1992   Polaschegg
5,163,909 A   11/1992  Stewart
(Continued)

FOREIGN PATENT DOCUMENTS

DE   19924031 A1   11/2000
EP   1267960 A2    1/2003
WO   02083207 A1   10/2002

OTHER PUBLICATIONS

International Search Report, of the International Searching Authority, dated Dec. 23, 2010, from Parent PCT/US2010/024430, Priority Date, Feb. 17, 2009.
(Continued)

*Primary Examiner* — Rebecca E Eisenberg
(74) *Attorney, Agent, or Firm* — Janine M. Susan; Burns & Levinson LLP

(57) ABSTRACT

The invention relates generally to implantable drug delivery devices. Devices having a single drug chamber configuration, a divided drug chamber configuration and a compact dual-drug configuration are described. The devices have features to prevent clogging of the dispensing catheter and the creation of a local vacuum caused by the dispensing of the drug fluid. Also provided are features of a failsafe refilling process, automatic refill notification, and performance verification process. The divided drug chamber configuration enables frequent or continuous minute doses. A dual-drug chamber configuration uses self-locking refill containers to prevent mismatching between refill containers and drug chambers.

3 Claims, 21 Drawing Sheets

(51) Int. Cl.
*A61M 5/14* (2006.01)
*A61J 1/06* (2006.01)
*A61J 1/14* (2006.01)
*A61M 5/168* (2006.01)
*A61M 39/02* (2006.01)
*A61M 5/145* (2006.01)

(52) U.S. Cl.
CPC ............... *A61M 2005/14513* (2013.01); *A61M 2039/0238* (2013.01); *A61M 2205/14* (2013.01); *A61M 2205/3317* (2013.01); *A61M 2205/3389* (2013.01); *A61M 2205/3515* (2013.01); *A61M 2205/50* (2013.01); *A61M 2205/70* (2013.01); *A61M 2209/045* (2013.01)

(56) References Cited

U.S. PATENT DOCUMENTS

| | | | |
|---|---|---|---|
| 5,707,361 | A | 1/1998 | Slettenmark |
| 5,798,114 | A | 8/1998 | Elsberry et al. |
| 7,338,260 | B2 | 3/2008 | Brundle |
| 7,867,221 | B2 | 1/2011 | Haase |
| 2005/0197649 | A1 | 9/2005 | Shelton et al. |
| 2007/0255259 | A1 | 11/2007 | Miesel |

OTHER PUBLICATIONS

Written Opinion of the International Search Authority, dated Dec. 23, 2010, from Parent PCT/US2010/024430, Priority Date, Feb. 17, 2009.

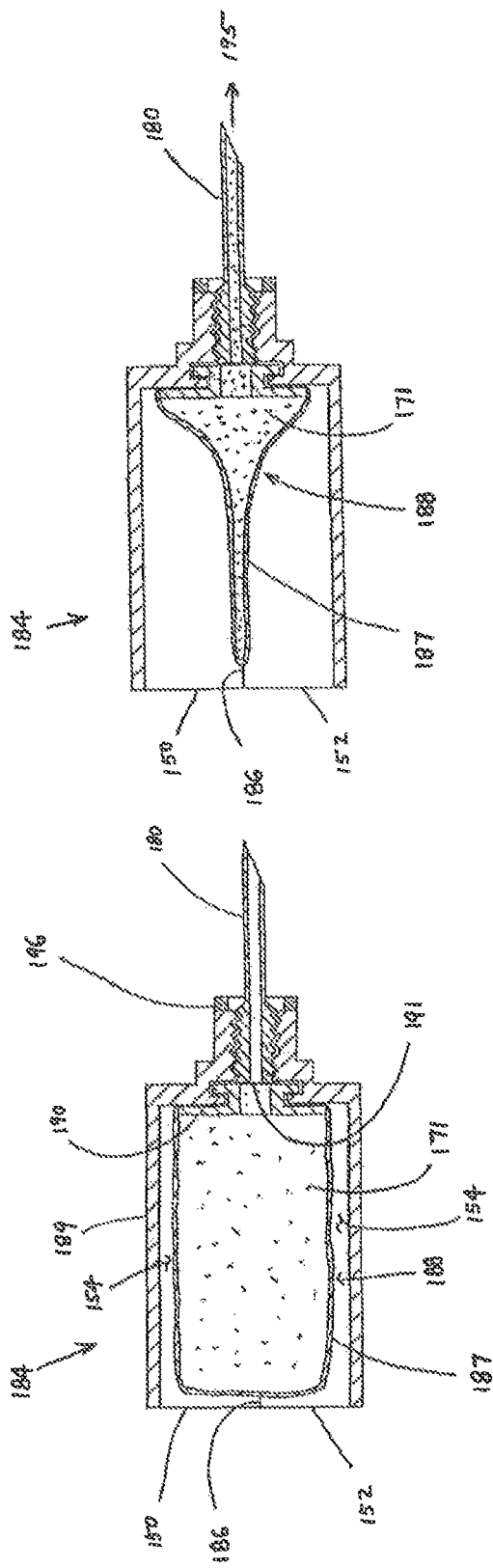

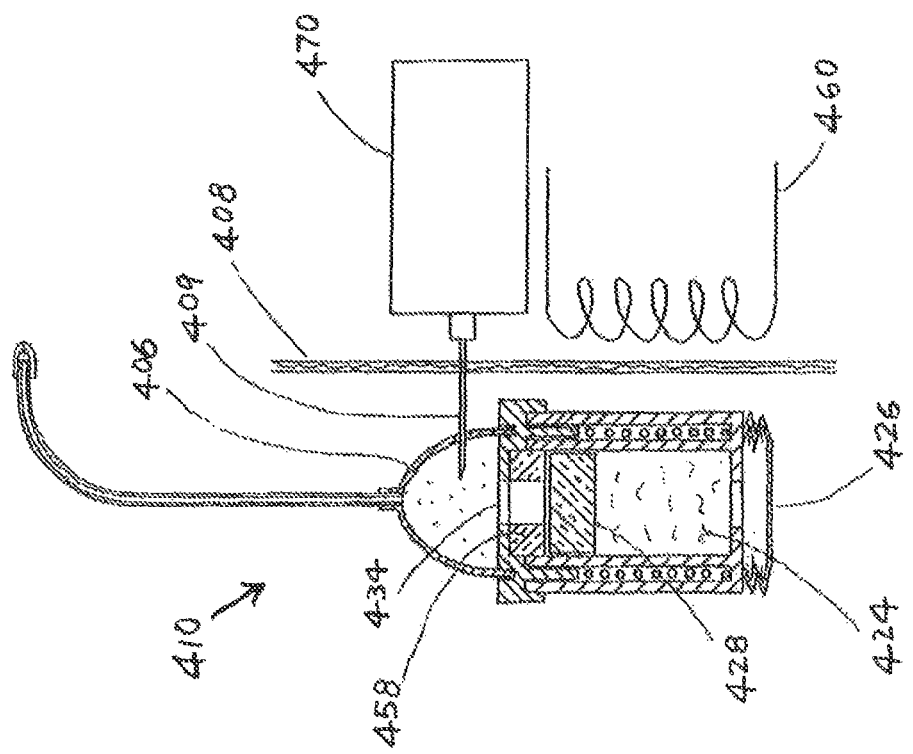
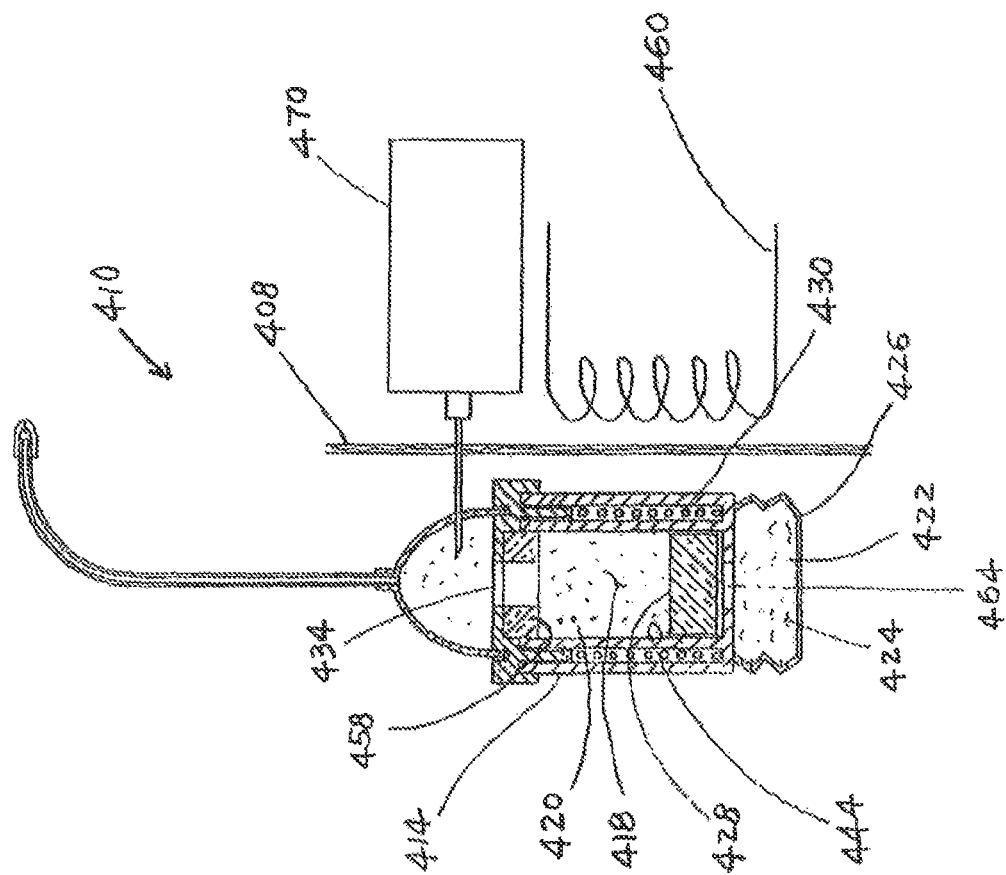

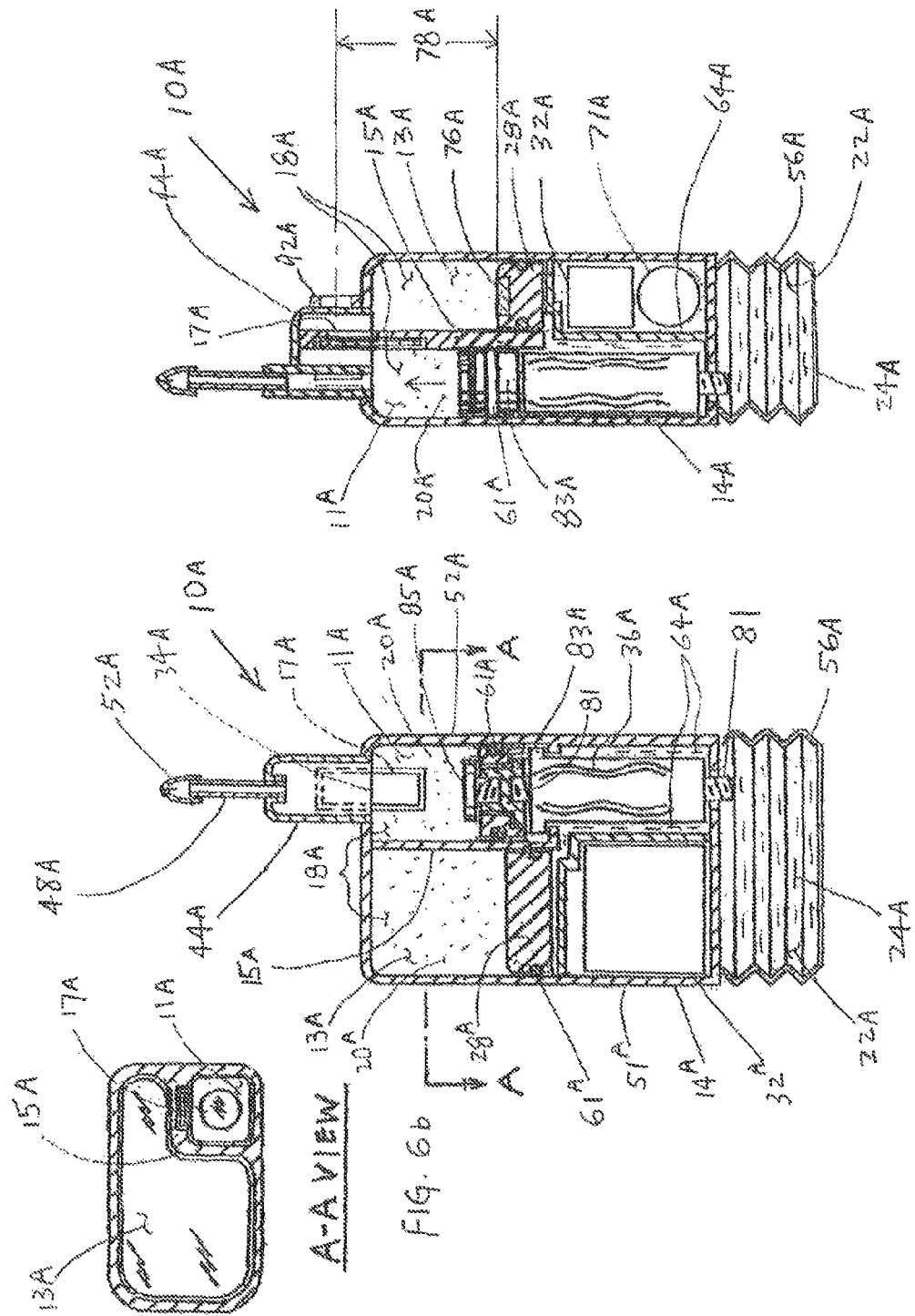

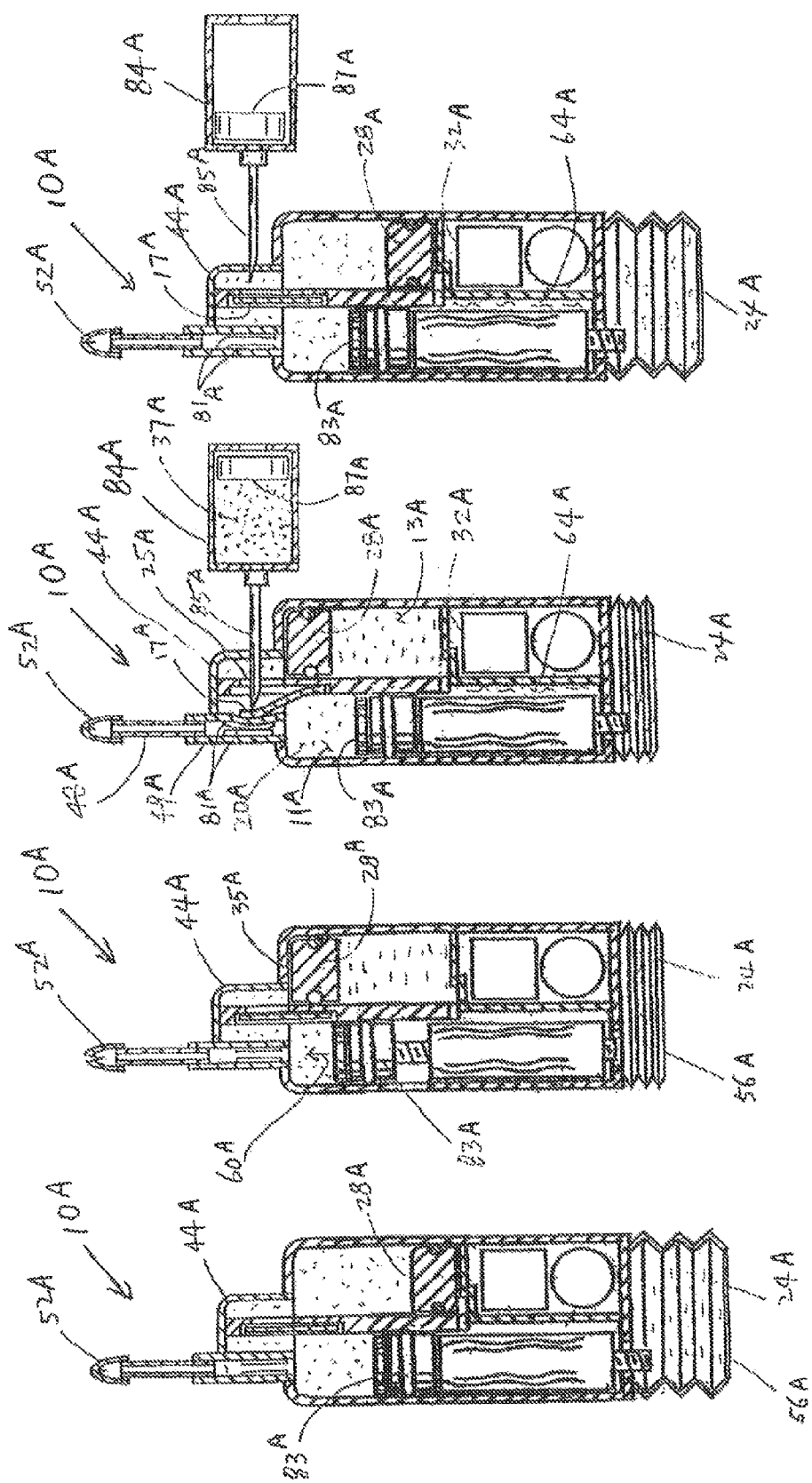

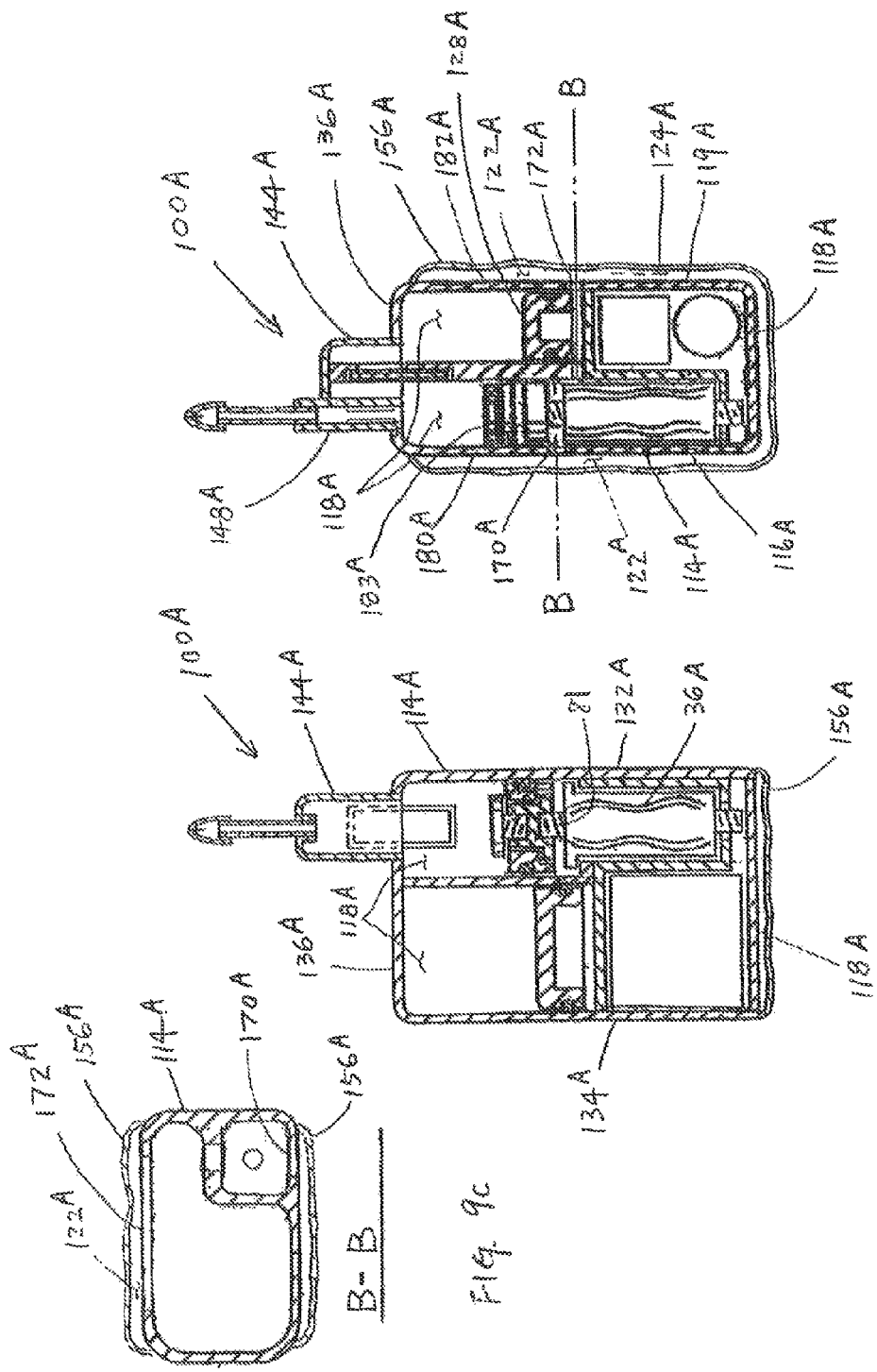

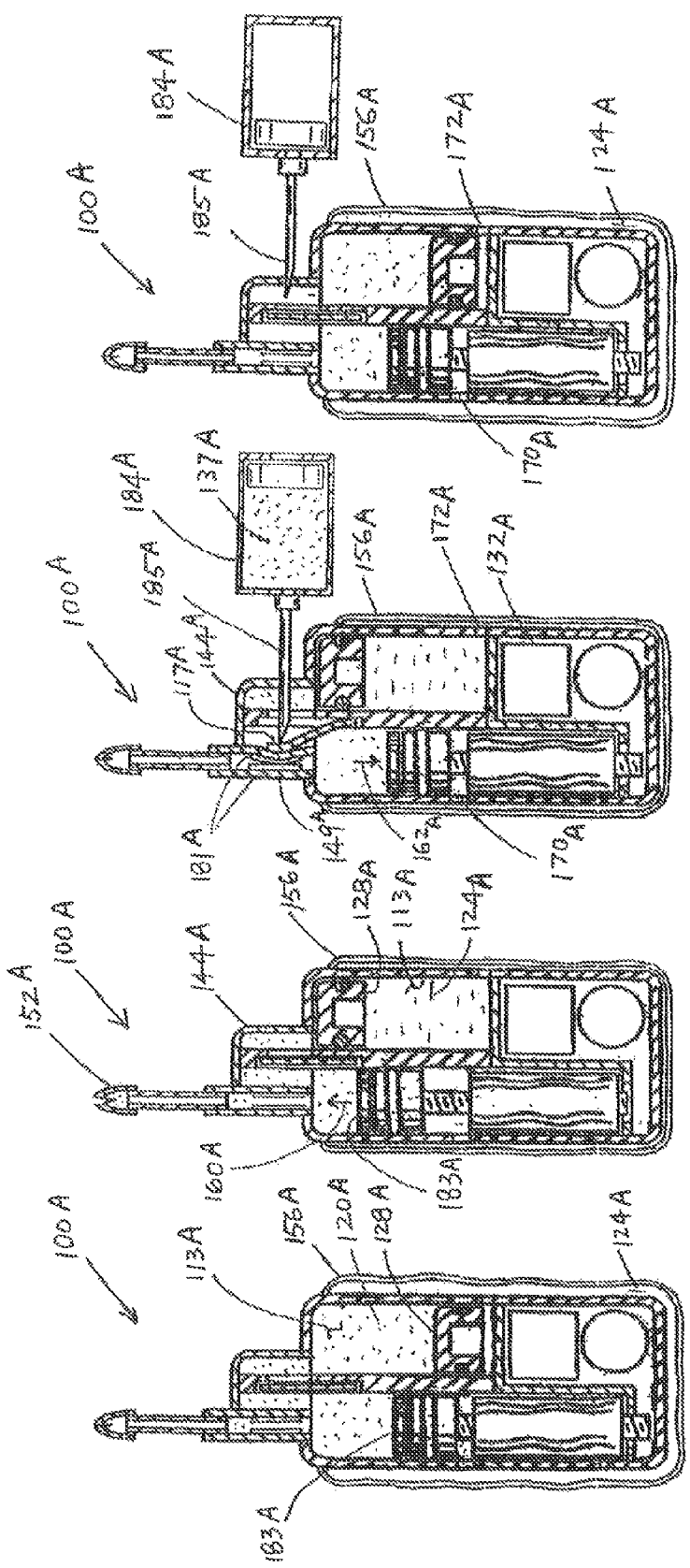

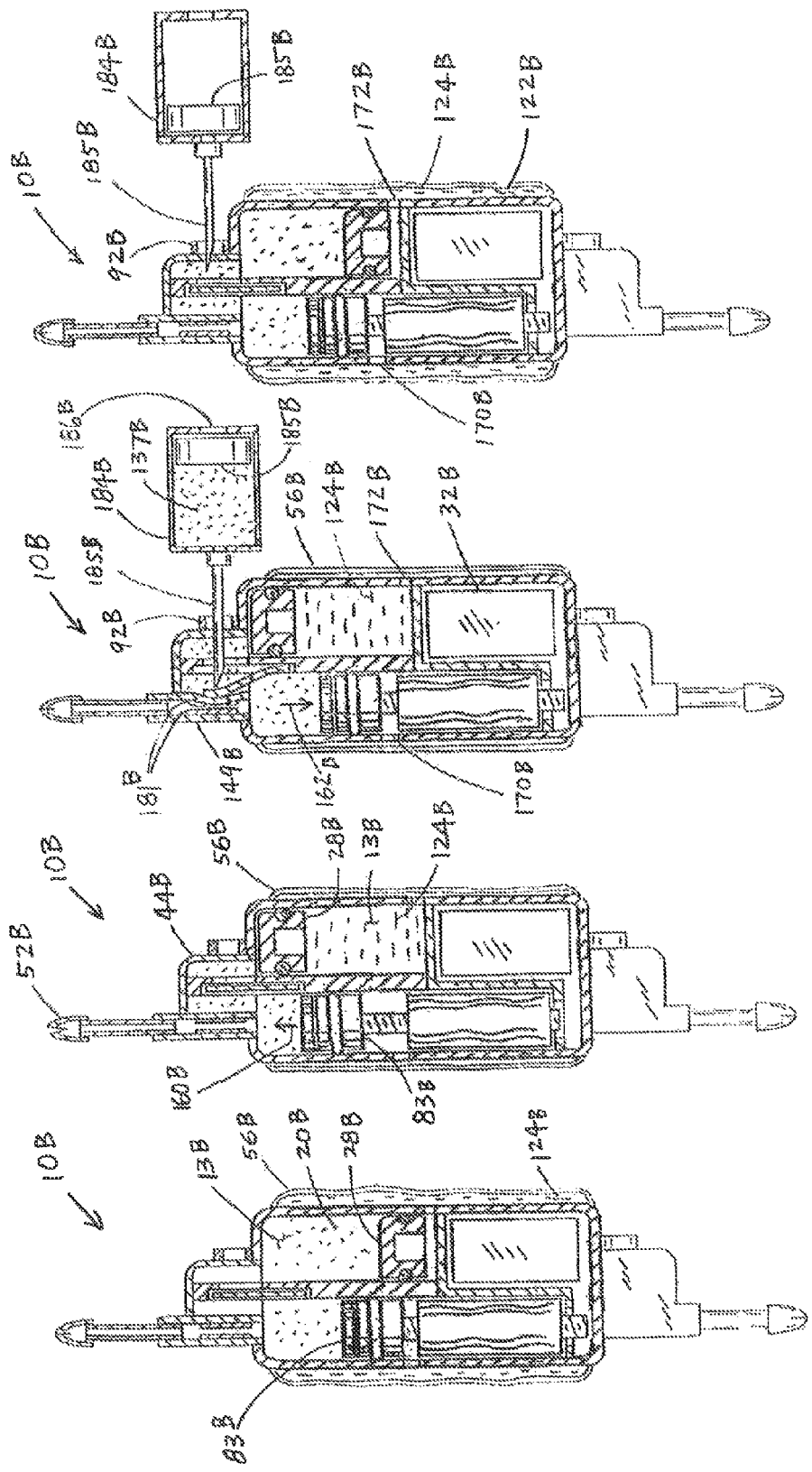

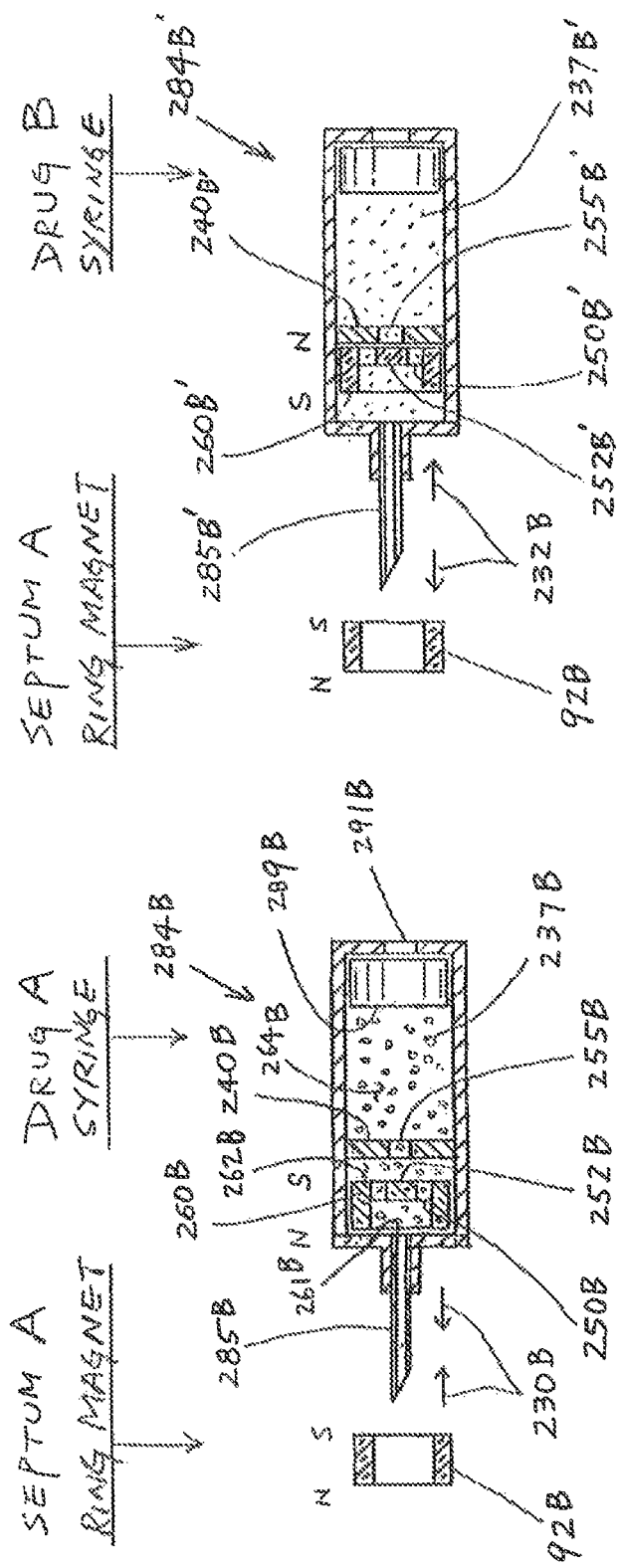

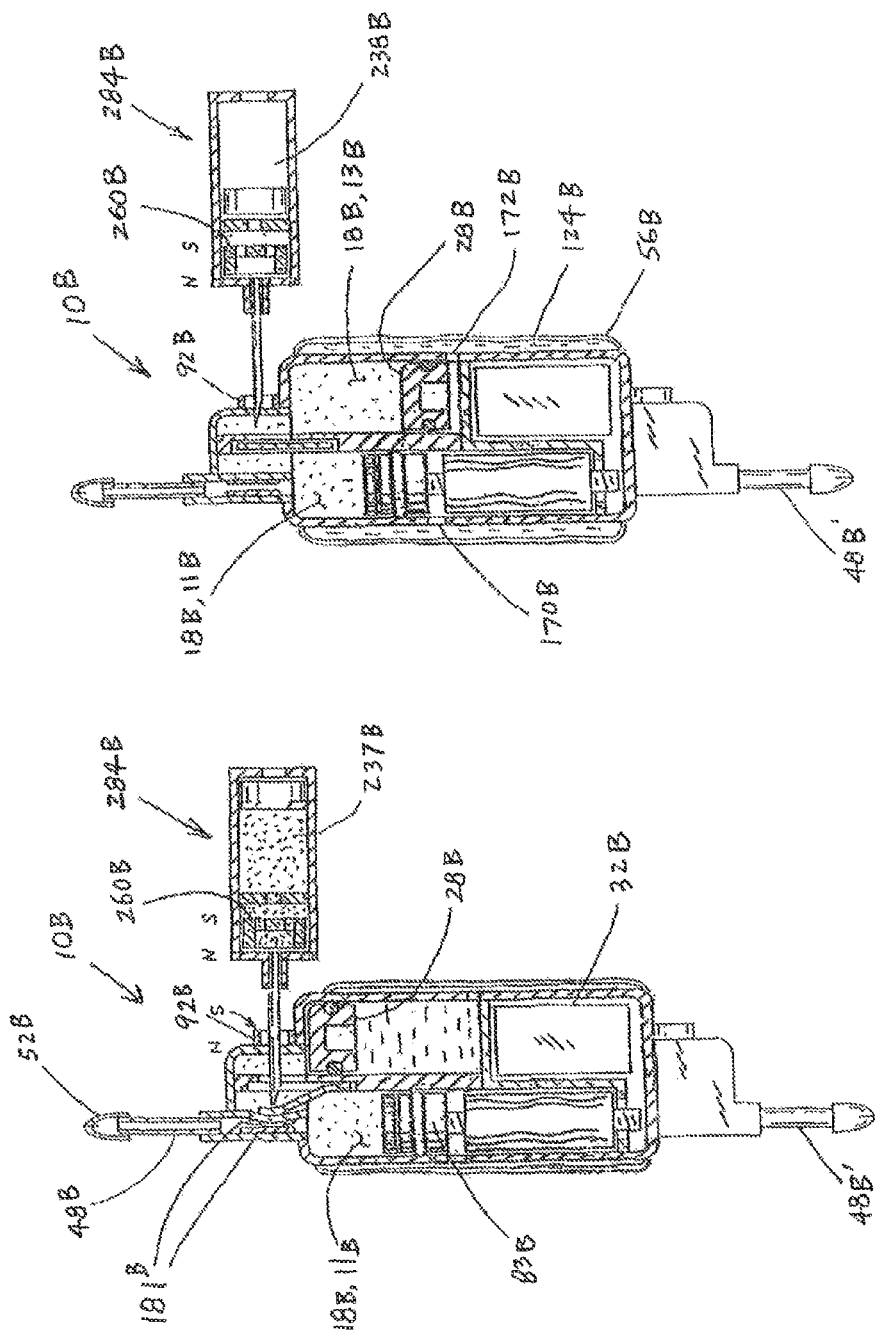

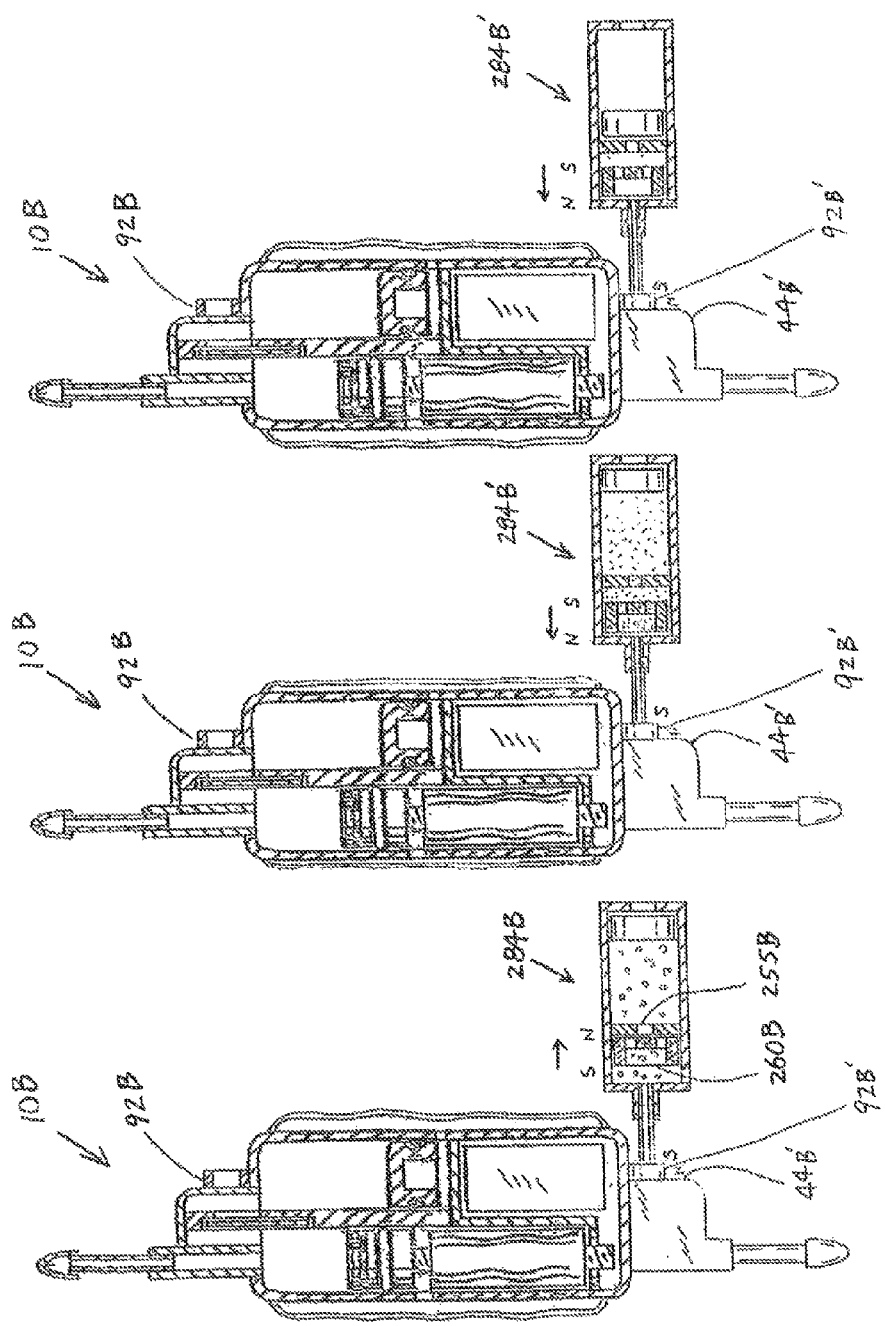

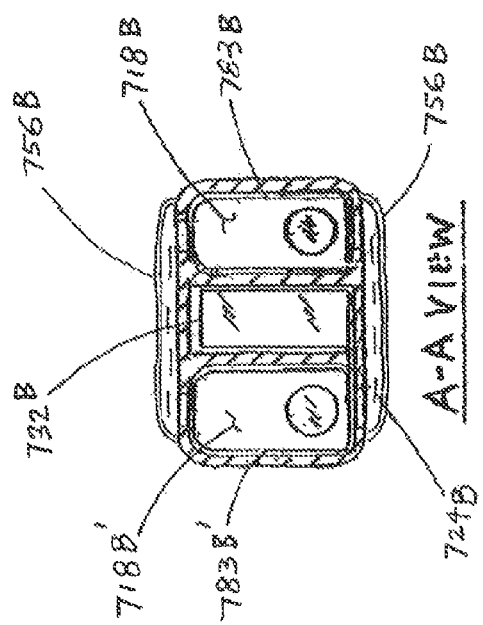
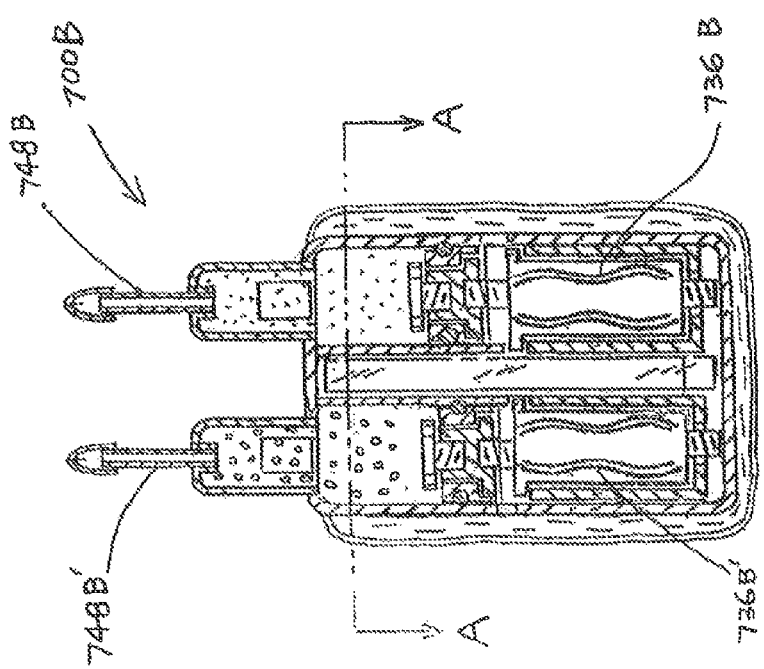
FIG. 18b
FIG. 18a

IMPLANTABLE DRUG DELIVERY DEVICES

FIELD OF THE INVENTION

This invention relates to implantable and refillable drug delivery devices with programmable features.

BACKGROUND

Drug delivery by means of injections, inhalation, trans dermal or swallowing pills or capsules generally results in varying drug concentrations between dosings. Many diseases would be better treated if the therapeutic drug were given so as to obtain a more or less constant drug level in the region of interest, especially if systemic drug concentrations could be maintained at or near zero thereby minimizing side effects. Implantable drug delivery devices attempt to achieve this by delivering small amounts of drug to a specific body cavity on a frequent basis. These delivery systems also are capable of protecting drugs which are unstable in vivo and that would normally require frequent dosing intervals. Implantable drug delivery devices include polymeric implants, implantable osmotic pump systems, and micro-pumps.

Polymeric implants, used extensively in controlled drug delivery systems, include nondegradable polymeric reservoirs and matrices, and biodegradable polymeric devices. In both cases the drug is released by dissolution into the polymer and then diffusion through the walls of the polymeric device. The release kinetics of drugs from such systems depends on both the solubility and diffusion coefficient of the drug in the polymer, the drug load, and, in the case of the biodegradable systems, the in vivo degradation rate of the polymer. Examples of polymeric implants include simple cylindrical reservoirs of medication surrounded by a polymeric membrane and homogeneous dispersions of drug particles throughout a solid matrix of nondegradable polymers. Biodegradable polymeric devices are formed by physically entrapping drug molecules into matrices or microspheres. These polymers dissolve when implanted or injected and release drugs.

Another method for controlled prolonged delivery of a drug is the use of an implantable osmotic pump. An osmotic pump is generally in a capsule form having permeable walls that allow the passing of water into the interior of the capsule containing a drug agent. The absorption of water by the water-attracting drug composition within the capsule reservoir creates an osmotic pressure within the capsule to push the drug out of the capsule to the treatment site.

Implantable micro-pumps for drug delivery applications usually include a permeable membrane for controlled diffusion of a drug into the body from a suitable reservoir. Such devices are limited in application primarily since the rate at which the drug is delivered to the body is completely dependent upon the rate of diffusion through the permeable membrane. With these devices the rate of drug delivery to the body may be affected by differing conditions within the body. In addition, such systems make no provision for the adjustment of the rate or time interval for drug delivery, nor can the delivery rate be easily varied.

Although polymeric implants, osmotic pumps and micro-pumps may provide a relatively steady rate of drug release, some drugs are more effective given in intervals. Implantable infusion pumps can be programmed to deliver drugs at very precise dosages and delivery rates. These pumps may have a feedback device that controls drug delivery according to need. With the current development of electronics and miniaturization of pumps and sensors, various vital signs can be monitored leading to feedback systems such as for monitoring blood glucose levels and delivering insulin when needed. The size of the pump depends on the amount of drug and the intended length of treatment. A barrier in feedback technology in using an implantable sensor is the problem of body proteins causing reduced sensitivity of the sensors, compromising the reliability of the sensor input.

There are many existing examples of implantable medical device applications. Implantable insulin pump technology has been developed with a goal of simulating the normal function of the pancreas by using glucose sensors and the predictive mathematical models. The sensors would assess the level of glucose in the blood and pass the information to a control algorithm used in a microprocessor chip for causing appropriate action by the pump. Such a device delivers a dose of insulin through a catheter into a patient's abdominal cavity. According to one manufacturer a disk-shaped pump weight of about 5 to 8 ounces when filled can hold an insulin supply adequate for several months and can be refilled with a syringe injection across abdominal tissue with battery life lasting about eight to 13 years. This delivery system keeps the liver from secreting excess glucose (blood sugar) into the bloodstream. Current pump technology difficulties include blockage of the catheter, infection at the implantation site, as well as accidentally injecting insulin refills into patient's abdomen instead of the pump reservoir. A typical reservoir in an implantable pump is to be refilled every three months.

For pain relief, drug delivery devices include the SynchroMed, an externally programmable implantable device for the administration of morphine sulfate to treat chronic pain, and the AlgoMed, designed to treat intractable pain in cancer patients. The AlgoMed device includes a drug reservoir implanted just under the skin of the abdomen, and a small catheter that delivers medicine to the spinal cord.

The treatment of glaucoma presents several strong challenges to drug delivery implant technology due to the sensitivity of the eye which therefore requires more frequent and precise dosing of medication while the small anatomical space limits the size of an ocular implant device. The surface of the eye is a significant physical barrier to medications that target intraocular treatment sites. Topical eye drops must be able to permeate through the modified mucosal membrane that covers the cornea. Only a very small percentage (~5%) of the eye drops actually reach the intraocular space. While drugs that are released rapidly produce a relatively rapid and high concentration in the body, followed by a sharp decline, it is preferable to have controlled-release systems deliver a drug at a slower rate for a longer period without manual application by patients. In many glaucoma treatments, two drugs are used; a first drug for reducing internal pressure inside the eye and a second drug for reducing side effects. It is, therefore, desirable to have a compact drug delivery device that can dispense two drugs with separate dispensing controls.

To improve the reliability and safety of an implantable drug delivery pump device, it is desirable to have a pump with a catheter with positive closing and a failsafe refilling process eliminating any possibility of injecting drug into a body cavity during the refilling process, an automatic notification feature to alert the patient of the need to take timely refilling action, as well as a process for verifying the performance of the pump. Preferably all of these desirable features can be achieved in an implantable drug delivery pump device using an implantable battery and without using an external controller.

To maintain a more constant rate of dispensing drug dosages, it is desirable to have an implant pump capable of precisely delivering a small amount of drug volume in the nano-liter range at each step of piston movement. It is desirable to infuse such minute dosages at time intervals appropriate for sustaining drug efficacy while avoiding side effects. And it is desirable to have an automated refilling process to prevent the injection of drug outside the implant pump into body tissues while refilling the pump.

The following references describe implantable devices.

U.S. Pat. No. 6,497,699 by Ludvig, et al. describes a miniature apparatus for the treatment of brain disorders. The apparatus is a combination of electronic and pharmacological devices placed and powered entirely within the human body. A neuroprosthesis monitors the electrical activity of a dysfunctioning brain area and delivers drug molecules into the problem area. The apparatus includes a refillable drug pump; a recording electrode for outputting an electrical signal characteristic of an electrical activity of the brain; and a microcontroller to control the dispensing of the drug based on the electrical signal. The timing and duration of the drug deliveries are determined by the feedback of the brain's own electrical activity. The invention describes an application of an implantable pump having multiple dispensing outlets for targeting different problem areas. However, no specific pump design is mentioned.

U.S. Pat. No. 5,832,932 by Elsberry, et al. discloses techniques and apparatus for infusing drugs into the brain to treat movement disorders. The invention employs an implantable pump and a catheter for infusing therapeutic dosages of the one or more drugs into the brain at treatment sites. A sensor for detecting the extent of the abnormal motor behavior may be used in combination with the implantable pump and catheter. The therapeutic dosage is adjusted according to signal input of the sensor to decrease the abnormal motor behavior. According to the patent the method is applicable to treat the symptoms of hypokinetic disorders, such as Parkinson's disease, and hyperkinetic disorders, such as Amyotrophic Lateral Sclerosis, Huntington's Disease, Ballism or Dystonia. The application of drug delivery device for treating movement disorder by brain infusion and the method of using a sensor for motion feedback for adjusting drug dosage in an implantable pump device are incorporated by reference.

For ophthalmic applications, U.S. Pat. No. 6,976,982 by Santini, Jr., et al. and U.S. Pat. No. 7,455,667 by Uhland, et al. provide a flexible microchip drug delivery device that attaches to the curved surface of an eyeball. The ophthalmic microchip device is in the form of an array of drug-containing microchips that are attached to a flexible supporting layer conforming to the backside surface of an eye. Release of the contents of each microchip reservoir is controlled by diffusion through, or disintegration of, the reservoir cap. The reservoir cap can be an anode made of thin film gold in electrical communication with a cathode in the device. When an electric potential of approximately 1 volt is applied the reservoir cap is oxidized to facilitate its disintegration, exposing the reservoir contents to the surrounding fluid. A microprocessor is preprogrammed to release drug from specific reservoirs by directing power from a battery to specific reservoir caps. Once released, the drug is in contact with the surface of the eye and diffuses into the eye. The reservoir activation can also be conducted wirelessly by telemetry with electromagnetic or optical means. An optical means can use an ophthalmic laser to activate LED receivers in the device. However, a potential problem with these devices is that the dissolved cap material is not removed and may even "re-solidify" when the power for dissolving the cap material is off.

The invention of U.S. Pat. No. 7,181,287 by Greenberg deals with retina stimulation by electrodes or by drug to enable vision in blind patients or treatment of a chronic condition. Specifically it is directed to an implantable device to enable delivery of drugs to the retina for stimulating the retina. The drug delivery device is secured by a tack to the retina at a desired location without damaging the retina and it is out of the field of vision from the lens to the retina. The device may be a passive osmosis type in the form of a hollow flexible polymeric pillow containing drug for slow release to deliver drugs through multiple orifices to the desired treatment sites. The device may also be an active pump type receiving drug from a reservoir transferred by a pressure development device through a tube with the flow rate controlled by a micro-valve. The microvalve, the pressure development device and the reservoir are attached to the sclera outside the eye under the conjunctiva for ease of refilling of the reservoir. Also by the same author, U.S. Pat. No. 7,483,750 specifically discloses preferred position of a retinal device and the connection between a device reservoir and the retinal device for avoiding damaging to the retina. The retinal implant is implanted subretinally at the back of the eye near the fovea between the photoreceptor cell layer and the retinal pigment epithelium. The conduit connects the retinal implant with the drug reservoir transretinally through retinal incision and the vitreous cavity. The preferred retina incision is at a location near the front of the eye where there is no retina to avoiding damage to the nutrient rich choroid and disruption of the blood supply to the retina. These two patents provide applications and suitable location of a drug delivery device for treatments of chronic eye conditions and indicate the feasibility of separating the small-size drug pillow positioned inside the retina layer from the larger size pump body positioned outside the eye. However, the patents do not address the mechanism of dispensing the drug in controlled manner. The use of an implantable pump for treating retinal diseases is incorporated by reference.

U.S. Pat. No. 6,077,299 by Adelberg, et al. deals with a non-invasively adjustable valve implant for the drainage of aqueous humor in glaucoma. The implant valve is a rotor-type device with the valve opening controllable by a magnetic field through an external instrument. The glaucoma valve of the invention overcomes the excess absorption problem of a newly implanted pump in a treatment area, where the aqueous humor is readily absorbed into the Tenon's tissue overlying the implant. Excess absorption can cause the pressure within the eye to fall to an unacceptably low level damaging eyesight. A higher pressure set-point can be made in the implant valve for the first few days after surgery to minimize the risk of the complications. The implant valve can also be adjusted to compensate for changes due to partial occlusion of the inlet tube by particulate matter and infiltration by body tissue. However, the valve implant of this invention is not a pump for dispensing drug. Nevertheless, the patent shows that non-invasive adjustability is required for an implant device.

For ocular drug delivery, U.S. Pat. No. 3,618,604 by Ness discloses a drug-dispensing ocular insert to deliver drug to the eye over a prolonged period of time. The ocular insert is comprised of either a flexible body of polymeric material or a sealed container having membrane walls insoluble in tear liquid and having an imperforate surface. The drug contained in the insert is diffused at a controlled rate through the polymeric material or the membrane walls to the eye in a therapeutically effective amount. The ocular insert is to be placed in the cul-de-sac of the conjunctiva between the sclera of the eyeball and the lower lid. The inserts depend on osmotic pressure difference to control drug delivery and they are not personalized for individual needs. Their diffusion rates are not changeable once installed. An implant pump with programmable timed release is desirable and to enable more varied applications.

U.S. Pat. No. 7,377,907 by Shekalim provides an insulin pump that supplies insulin in a pre-pressurized chamber through a flow control valve. Precise metering is achieved by a piezoelectric actuator. The insulin in the chamber is pressurized and dispensed by a piston, which is driven by a biased spring. The device also includes a pressure regulator, a removable cartridge unit containing a pre-pressurized fluid reservoir, and an electronic package for the programming of basal rates. Nevertheless, patients with a portal device are at risk for trans-cutaneous infections.

To ensure positive closure at the dispensing opening, U.S. Pat. No. 5,997,527 by Gumucio, et al. provides a drug delivery capsule device comprising an osmotic-agent chamber having a semi permeable membrane wall, a drug chamber attached with a slit valve, and a moveable piston separating the two chambers. Under an osmotic pressure created in the osmotic chamber, the piston pushes drug through the slit valve. Being exposed to the body tissue environment the permeable membrane wall of the osmotic chamber wall allows body fluid to pass into the capsule by osmosis to create an osmotic pressure to drive the piston. The osmotic capsule of this invention lacks active control for ensuring positive closing of the slit valve. In operation, the osmotic pressure varies with the movement of the piston and the remaining quantity of the drug in the drug chamber. At one end, an excessive osmotic pressure can keep the slit valve at open state with continuous dispensing with a possibility of overdosing. At the other end, an insufficient osmotic pressure cannot drive the piston to open the slit valve resulting in no drug being dispensed. This unreliable drug delivery due to lack of active control can cause discomfort and adverse side effects in the patient.

On the use of two fluidic drug chambers, U.S. Pat. No. 5,607,418 by Arzbaecher provides an implantable drug delivery device having a deformable dispensing chamber within a deformable reservoir chamber. In this configuration, the dispensing flow rate of the dispensing chamber is designed to be greater than the refilling flow rate from the reservoir chamber and that the reservoir chamber automatically refills the dispensing chamber following discharge of a dispensing portion of the fluidic drug. Because the dispensing rate is greater than the refilling rate across the internal valve between the two deformable chambers, a partial vacuum may be created in the two chambers resulting in a poorly controlled dispensing rate or interruption of the dispensing flow to the treatment site. The deformable dispensing chamber within a deformable reservoir chamber cannot ensure that the drug flow rate in and out of the dispensing chamber and the reservoir chamber are equal.

U.S. Pat. No. 4,883,467 by Franetzki addresses the problem of gas bubbles in pumping medication fluid in a conventional implantable medication device using a reciprocating piston pump wherein the medication reservoir is typically under atmospheric pressure between 0.5 and 1.0 bar. Gas bubbles may be generated in pumping the medication fluid at below ambient pressure or during refilling of the medication reservoir. In the reciprocating motion in the pump chamber a gas bubble would be merely compressed and decompressed without being transported out of the device, making the infusion performance of the device unreliable. This under-pressure pumping is less a problem in larger pumps having a displacement volume greater than 10 microliters. But the existence of dead space in the pump chamber of a small pump is compounded because the size of the dead space may be comparable to the size of the displacement volume of the piston. In this case, pumping medication containing gas bubbles may become impossible particularly at the lower limit of the under-pressure (0.5 bar). This patent provides an implantable medication device using a magnetized reciprocating piston and a magnetic check valve for pumping medication fluid containing gas bubbles to achieve a satisfactory infusion rate such that the patient would receive medication without interruption by the gas bubbles. The piston contains a magnetic material which can be driven by a magnetic means to move the piston forward for dispensing and a separate magnetic means for moving the piston backward. The magnetic check valve is normally biased to block fluid flow.

Addressing the problem of gas bubble formulation, U.S. Pat. No. 7,201,746 by Olsen provides an implantable therapeutic substance delivery device having a piston pump with an anti-cavitation. The device has an inlet chamber and a pumping chamber. In the pumping chamber a piston having a permanent magnet is driven by the magnetic fields created by two separate inductive coils which impart a reciprocating motion to the piston to pump fluid from the pumping chamber into an outlet. In such a pump chamber the backflow of fluid from the inlet chamber can decrease pressure in the pumping chamber causing gasses to come out of solution when the pumping chamber is being filled with the fluid. The invention provides an anti-cavitation valve that is configured to open when the therapeutic substance inlet pressure exceeds the inlet chamber pressure and to close when the inlet chamber pressure exceeds the therapeutic substance inlet pressure. The objective of the anti-cavitation valve is to prevent the pumping chamber pressure from decreasing below a predetermined low pressure level during piston retraction and to enable more complete filling of the pumping chanter when the piston is retracted.

Both U.S. Pat. Nos. 4,883,467 and 7,201,746 utilize a magnetized piston driven by magnetic forces and attempt to suppress gas bubble formation by using biased valve mechanisms to increase the pressure in their pump chambers. However, without positive mechanical control of the piston, the piston movement under the magnetic forces depends on the pressure level in the pump chamber, which may vary in operation. Also, the compressed gas bubbles inside the pump chamber may expand when released at the device exit at the treatment site. Furthermore, these device configurations inherently entrap gas pockets and allow for the existence of dead space which is a major source of the pumping problem.

US Patent Application 20080287874 by Elmouelhi controls the dead volume of a piston pump by using an adjustment screw. The infusion pump device is of a reciprocating magnetized pistontype driven by solenoid coils. Typical manufacturing tolerances in the production of the pump components may result in unwanted dead space in the pumping chamber. The dead space includes space that the piston does not reach at the limit of its forward movement that leads to trapped air bubbles not displaced during the pumping strokes, the pumping volume of the piston may not be accurate as the piston movement may result in the compression of the air bubbles rather than displacement of the fluid. The invention solves the problem by adjusting the end position of the piston's forward stroke with an adjustment screw allowing for selective elimination of the dead volume and precise adjustment of the fluid pumped. Similarly US Patent Application 20080269682 by Kavazov et al. address the reservoir air bubble problems of a magnetized reciprocating piston pump by modifying the geometry of the plunger or the reservoir of the pump device. In various embodiments of the invention, a reservoir, a plunger head which moves within the reservoir, or both the reservoir and the plunger head are shaped to form a bubble trap region for trapping air bubbles so as to limit the presence of air bubbles in a fluidic medium expelled from the reservoir. Both of these patents recognize the existence of dead volume due to the structure of its piston pump device and attempt to minimize the air bubble problems. However, a piston pump that eliminates dead volume such that no air bubble problems exist would be preferable.

On refilling, U.S. Pat. No. 7,347,854 by Shelton, et al. relates to a process of refilling an implantable drug delivery device. The controller in accordance with this invention is programmed to determine the volume of the old drug remaining in the reservoir. The controller then monitors the subsequent delivery of the old drug to the patient to determine when the remaining old drug has been cleared from the device. Accordingly, the controller adopts a new dispensing profile for the drug refilled into the reservoir. The process as described in this patent is limited to the general practice of adding new drug after using up the original drug in the reservoir. No specific refill steps such as retracting a piston, closing a dispensing tip and using a passive syringe are addressed. In fact, a programmable pump allows changing the dispensing profile at any time depending on the need of a patient prior to using up the existing drug in the reservoir.

An implantable drug delivery pump of U.S. Pat. No. 6,283,949 by Roorda discloses a method of dispensing drug at a controllable rate from a reservoir. The pump includes a reservoir, a dispensing chamber, a compressible dispensing tube attached to the dispensing chamber, and a rotating-arm actuator for applying a compressive force onto the dispensing tube to deliver the drug through a catheter. The rotating-arm actuator allows additional drug drawn into the dispensing tube from the reservoir, which can be refilled. A one-way intake valve is used and the reservoir can be refilled through a septum. In this method, rotational actuator compressive force is used and the reservoir is limited to a circular configuration to accommodate the rotating arm. The patent does not address failsafe requirements for refilling a pump reservoir.

U.S. Pat. No. 4,784,646 by Feingold provides a subcutaneous delivery device for injecting drug to a local destination. The subcutaneous delivery device is mainly a catheter having a self-sealing port at the input end attached with an internal magnet and a valve at the output end. The catheter device further includes a corresponding external magnet, separated from the internal magnet by the skin, as a locator for magnetically adapting to the internal magnet. The attraction between the two magnets, which are annular magnets of opposite polarities, can facilitate positioning and stabilizing a syringe needle during injection. However, the syringe needle may still be inserted at wrong location and the drug in the syringe be injected by pressing the plunger of the syringe, therefore, causing damage to body tissues. Furthermore, the valve at the dispensing end of the device cannot be positively controlled for dosing as the internal pressure in the device may exceed the self-dosing pressure of the valve.

U.S. Pat. No. 7,044,932 by Borchard, et al. provides an access template for locating the refill septum of an implant drug pump. The needle insertion occurs without using radiological instruments for guidance. The access template comprises a denial surface, an access port, and template labeling. The denial surface has a periphery with a location diameter and an alignment feature. The denial surface is configured to prevent penetration through a dermal layer into the implantable drug pump. Using labels of the same color in both the template labeling and the needle labeling provides a means for ensuring the proper drug being administered but the system is not failsafe as negligence in matching colors may occur.

To locate an implantable pump for the purpose of refilling, U.S. Pat. No. 7,191,011 by Cantlon discloses the use of a port with light emitters. The light emitters can be arranged in various geometric forms and colors. Also disclosed are energy emitters such as light emitting diodes, edge emitting diodes, or VCSELs, and sonic emitters. The concepts as disclosed are not applicable for situations where light or sonic waves cannot be detected such as under the skull. Furthermore, U.S. Pat. No. 7,356,382 by Vanderveen describes a system and method for verifying that a particular fluid supply is connected to an infusion pump by means of an operator-induced pressure change. An upstream pressure sensor coupled to a fluid supply conduit provides pressure signals to a processor. In a verification mode, the processor receives the pressure sensor signals in comparison with an operator-induced pressure change in the conduit to verify that the particular fluid supply is connected to the infusion pump. The processor also prompts the operator to confirm the pressure change if the pressure change signal is not detected within a predetermined time period. However, use of an operator-induced pressure change is not fail-proof. An operator may enter incorrect pressure values or connect the wrong drug supply with a correct pressure signal. A fail-proof system is needed to eliminate a possibility of operator errors.

U.S. Pat. No. 7,212,863 by Strandberg uses a test magnet in a specified time period for external activation of an implantable medical device, which can be externally programmed within the specified time period. When the magnet is taken away the implant device returns to the normal mode of operation. The use of test magnets is a simple means of external control of the operation of an implant device without involving a complex programmable external controller. The method of using an external test magnet for activating an internal device is incorporated by reference.

On programming features, U.S. Pat. No. 6,381,496 by Meadows, et al. provides context switching features for changing the operational parameters of an implantable device. These features enable a patient to change the current set of operational parameters to another set of operational parameters. The ability to change the current operational parameter set (OPS) is accomplished by including memory circuitry within the implant device wherein a plurality of OPS's are stored. An OPS setting can be manually activated and transmitted to the implant device to replace the current OPS. The patent provides programmable features for changing operational parameter settings, but it does not address refill steps and failsafe features.

U.S. Pat. No. 5,814,015 by Gargano, et al. uses a software warning as a failsafe measure for preventing the infusion of a wrong drug. A processor driven syringe pump for two syringes in a housing unit is suspended from an N pole. Its software provides a number of feedback warnings and alarms. The syringe plunger is driven into the syringe barrel by a motor operated by a failsafe feature against a short circuit in a drive circuit element feeding continuous current into the pump motor. A pusher assembly for the syringe includes a split nut that can be rotated and released to enable proper positioning of the syringe. The two pumps are jointly programmable and operable to allow the automatic stopping of a first pump and starting of a second pump for extended sequential infusion. Although the warnings and the failsafe feature are provided by the software against a short circuit they do not guarantee prevention of the infusion of the wrong drug. An ideal failsafe feature should provide a means for automatically preventing the refilling of a drug chamber with an incorrect drug.

On drive means for imparting a piston or plunger motion a pump device, a piezoelectric motor driven by electric pulses can be used. U.S. Pat. No. 6,940,209 by Henderson provides a piezoelectric lead screw motor for driving an assembly that contains a threaded shaft and a threaded nut. Subjecting the threaded nut to piezoelectric vibrations causes the threaded shaft to simultaneously rotate and translate in the axial direction. A drive product based on the concept called Squiggle motor has been commercialized. The SQUIGGLE SQ-306 model is 10 mm in length and 4 mm in diameter, and achieves precision levels in the micron range. The motor's power efficiency enables long battery life, which is a critical factor for implanted medical devices. Its motor driver board including ASIC, resonant inductors, Boost circuit and FWID diode can be packaged into 10 mm×10 mm×1.5 mm size. The use of commercially available SQUIGGLE motor is incorporated by reference.

US Patent Application 20080108862 by Jordan; Alain et al. describes an implantable device comprising a stepper motor for driving with an oscillator and an external controller for monitoring and correction of the performance of the device by passive telemetry. The displacement of the actuator is proportional to the number of pulses given to the motor coils. The method requires the use of an antenna coil coupled with a RF-to-DC converter to convert received RF energy to a DC voltage. However, the antenna coil and the converter add to the size of an implantable pump. The use of stepper motor as a drive means is incorporated by reference.

Alternatively, a piston or a plunger in a pump device can be driven by induction coils. U.S. Pat. No. 7,331,654 by Horsnell, et al. provides a solenoid valve mechanism using induction coils for controlling the flow of fluid through the valve. The valve mechanism includes a plunger member for axial reciprocation within a tubular member supporting an electric coil for generating a magnetic field when an electric current passes through the coil. The plunger is made of an electromagnetic material and can be magnetized by a magnetic field. The reciprocating motion of the plunger is adapted to open or close a nozzle orifice for injecting fluid drops on demand, such as on ink jet printer applications. The patent provides an example of using induction coils for driving plunger movements for dispensing fluid. The use of induction coils as a drive means is incorporated by reference.

With the limitations of the current implantable infusion pump technology, it is an objective of the present invention to prevent clogging at the catheter exit and the creation of a partial vacuum inside the delivery device. It is an objective to provide a failsafe refilling process and an automatic notification feature for the patient to take timely action. Additionally, it is another objective to provide a drug chamber configuration to enable dispensing of minute precise drug volumes at high frequency or at a continuous mode. It is another objective to provide a compact drug delivery device to dispense two drugs without mis-matching during the refilling process.

SUMMARY OF INVENTION

The present invention includes three drug delivery device configurations. The first is a single drug chamber configuration. The second is a divided drug chamber configuration. And the third is a compact dual-drug configuration that can dispense two drugs independently.

An implantable single-drug delivery pump device of this invention comprises a first chamber attached with a catheter and containing a drug fluid, a second chamber containing a filler fluid, and a piston separating the drug fluid and the filler fluid. The filler fluid, which is inert to the drug fluid, is partially enclosed by a collapsible wall. The collapsible wall, which is represented by bellow wall, enables the filler fluid to follow the movement of the piston in filling in the space in the first chamber vacated by dispensing of the drug fluid. For positive-closing at the dispensing opening, a slit valve is attached to the catheter. The slit valve closes upon retraction of the piston. The piston is controlled by a driver means for undergoing small reciprocating motion at predetermined amplitude which does not allow dispensing of the drug but does prevent clogging at the slit valve.

The implant pump is refillable. The positioning of a syringe needle can be facilitated by the attraction between a first magnet mounted on the septum of the pump device and a magnet attached to the needle. The refill syringe is of a passage type without having an active plunger.

With the needle inserted, the retraction or backward movement of the piston draws the refill fluid from the syringe into the first chamber. Continuous retraction of the piston draws in the drug fluid from the syringe to fill the first chamber while the catheter entrance remains closed by a negative pressure drop developed in the filling process.

The refilling process starts when an activation detector is activated. The two-way movement of the piston is controlled to enable repeated opening and closing motions of the slit valve with a specified amplitude and frequency for preventing clogging without dispensing the drug.

For verification of the pump performance the piston is attached with a second magnet to enable measurement of the distance between the first magnet and the second magnet by an external magnetic proximity sensor positioned across the skin. The piston can be driven by a piezoelectric motor or a stepper motor with the use of a threaded rod for achieving linear displacement of the piston. Such a driver means is controlled by a microprocessor and powered by an implantable battery contained inside the pump device. Alternatively, a piston can be made of ferrite material for magnetization by induction coils installed in the pump housing. The induction coils may be powered and controlled by an external controller.

The control software in the microprocessor controller is programmed to provide Dispensing Mode, Refilling Mode, Notification Mode and Verification-Calibration Mode.

An alternative implantable single-drug delivery device includes a divided drug chamber having a reciprocating piston and a follower for intermittent dispensing of drug dosages and a failsafe needle-activation feature for automatic refilling of the drug chamber. Also provided are a bellows-type and a soft-layer-type filler-fluid chamber containing an inert fluid to fill the space evacuated by the movement of the piston and the follower to prevent forming a partial vacuum in the fluid chambers enabling reliable performance of the device.

A drug delivery device of the divided drug chamber configuration comprises a divided internal fluid chamber containing a first fluid and an external fluid chamber containing a second fluid that is enclosed partially by collapsible soft-layered walls. The internal fluid chamber is divided into a first compartment and a second compartment by a wall mounted with a one-way valve.

The first compartment has a piston connected to a driving means and the second compartment has a follower, which is in communication with the movement of the piston. The second fluid in the external chamber serves as a filler fluid in communication with the internal fluid chamber for filling the spaces behind the piston and the follower. Both the piston and the follower separate the second fluid from the first fluid.

The piston performs a reciprocating motion under the control of a motor driver which is preprogrammed. The piston is preferably driven by a high-resolution piezoelectric motor for a minimal advancement in the micrometer range per step. With a miniature piston size, the drug volume may be dispensed in the nano-liter range per piston step. During the forward motion of the piston the one-way valve is forced to close and the slit-valve at the end of the catheter is forced to open to dispense the drug fluid. During the backward motion of the piston a partial vacuum is created in the first compartment that causes the one-way valve to open and allow the drug fluid from the second compartment to enter the first compartment. Simultaneously, the forward and backward movements of the piston and the follower cause the filler fluid to flow in or out, respectively, from the spaces behind the piston and the follower. When the drug fluid is completely dispensed, the back spaces of the piston and the follower are full of the filler fluid.

Refilling of the first chamber is accomplished by inserting a refill container into the septum of the device to force the one-way valve to contact the opposing catheter wall, causing the attached electrode elements to activate the reciprocating motion of the piston. The reciprocating motion draws in the refill fluid to fill both the first compartment and the second compartment while the catheter entrance remains closed by the one-way valve. Similarly, a small reciprocating motion may be performed without dispensing drug fluid after the piston is retracted a predetermined distance enabling refill and battery low notifications.

An implantable dual drug delivery system of this invention features two drug chambers and the use of self-locking refill containers for failsafe refilling of drug fluids in the device.

A self-locking refill container utilizes a movable magnet valve and an orifice plate for locking and unlocking the flow of drug fluid inside the container reservoir. For a matched refill container, the polarity of its magnet valve creates an attraction force toward the magnet on the septum of the drug chamber. The attraction force moves the magnet valve away from the orifice plate to enable the flow of the drug fluid from the refill container reservoir into the drug chamber. For a mis-matched container, the polarity of the magnet valve creates a repelling force away from the magnet on the septum such that the magnet valve is moved to contact the orifice plate and block the drug flow.

Specifically a dual drug delivery device of the present invention has a first drug chamber containing a first drug fluid, a second drug chamber containing a second drug fluid and an external filler fluid chamber containing filler fluid. Each drug chamber is divided by a wall having a one-way valve into a first compartment and a second compartment. Each first compartment has a piston connected to a drive means and each second compartment has a follower, which is in flow communication with the movement of the piston. A small reciprocating motion may be performed without dispensing drug fluid after the piston is retracted for a predetermined distance for refill and battery low notifications.

The filler fluid chamber is attached externally to the drug chambers and it contains a filler fluid enclosed by collapsible soft layers. The filler fluid is for filling the space left by the movements of the pistons and the followers to prevent a partial vacuum inside the drug chambers that would hinder the movements of the pistons.

DESCRIPTION OF THE DRAWINGS

FIG. 2b is a side cross-section view showing insertion of the refill container needle of FIG. 2a into the implantable drug delivery pump device of FIG. 1a.

FIG. 2c is a side cross-section view of a refill container of the present invention showing a collapsible bag at expanded full state.

FIG. 2d is a side cross-section view of a refill container of FIG. 2c showing the collapsible bag at a collapsed state.

FIG. 4a is a cross section view of an implantable drug delivery pump device using induction coils with the drug reservoir at full state.

FIG. 4b is a cross section view of an implantable drug delivery pump device of FIG. 4a using an external controller for refilling.

FIG. 6a is a front cross-section view of an implantable drug delivery device having a divided drug reservoir and a bellows-type filler-fluid chamber.

FIG. 6b is a top cross-section view of FIG. 6a showing cross-section areas of the first and the second fluid compartments.

FIG. 6c is a side cross-section view of the implantable drug delivery device of FIG. 6a showing a one-way check valve.

FIG. 7b is an isometric exposed view of FIG. 7a.

FIG. 8a is a side cross-section view of the implantable drug delivery device of FIG. 6c showing the second compartment of the drug reservoir full with first fluid.

FIG. 8b shows the implantable drug delivery device of FIG. 8a with the second compartment of the drug reservoir full with filler fluid.

FIG. 8c shows the implantable drug delivery pump device of FIG. 8b with a refill container needle inserted and pressing against a contact switch.

FIG. 8d shows the implantable drug delivery pump device of FIG. 8b with a refill container needle being removed from the one-way valve in the drug reservoir.

FIG. 9a is a front cross-section view of an implantable drug delivery device attached with a softlayer filler-fluid chamber.

FIG. 9b is a side cross-section view of the implantable drug delivery device of FIG. 9a showing soft-layer filler-fluid chamber attached to the housing wall of the device.

FIG. 9c is a B-B cross-section of FIG. 9b showing flow gaps for filler fluid on housing walls.

FIG. 10a is a side cross-section view of the implantable drug delivery device of FIG. 9b showing the second compartment of the drug reservoir at full state.

FIG. 10b shows the implantable drug delivery device of FIG. 10a with the second compartment of the drug reservoir full of filler fluid.

FIG. 10c shows the implantable drug delivery device of FIG. 10b with a refill container needle inserted and pressing against a contact switch.

FIG. 10d shows the implantable drug delivery device of FIG. 10c with a refill container needle being removed at completion of refilling.

FIG. 12a is a front cross-section view of an implantable dual drug delivery device with two dispensing valves at opposite sides of the device.

FIG. 12b is a top cross-section view A-A of FIG. 12a.

FIG. 12c is a side cross-section view of the implantable infusion dual drug delivery device of FIG. 12a.

FIG. 14a is a side cross-section view of the implantable dual drug delivery device as shown in FIG. 12c indicating the second compartment of the first drug reservoir full with first fluid.

FIG. 14b shows the implantable dual drug delivery device of FIG. 13a with the second compartment of the first drug reservoir full with the filler fluid.

FIG. 14c shows the implantable dual drug delivery device of FIG. 13b with a refill container needle inserted and pressing against a contact switch in the first catheter.

FIG. 14d shows the implantable dual drug delivery device of FIG. 13b with a refill container needle being removed from the one-way valve in the first drug reservoir.

FIG. 15a shows refill container of Drug A unlocked internally with matched septum of Drug A.

FIG. 15b shows refill container of Drug B locked internally due to mix-matching with the septum of Drug A.

FIG. 16a is an implantable dual drug delivery device of FIG. 15b with the refill container of Drug A unlocked internally when inserted into the septum of Drug A.

FIG. 16b is an implantable dual drug delivery device of FIG. 16a with the spent refill container removed from the septum upon completion of refilling.

FIG. 17a is an implantable dual drug device of FIG. 16a with the refill container of Drug A internally locked as inserted into the septum of Drug B.

FIG. 17b is an implantable dual drug delivery device of FIG. 17a with the refill container of Drug B unlocked internally when inserted into the septum of Drug B.

FIG. 17c is an implantable dual drug delivery device of FIG. 17b with the spent refill container removed from the septum upon completion of refilling.

FIG. 18a is a front cross-section view of an implantable dual drug delivery device with two drug chambers oriented in the same direction.

FIG. 18b is a cross-section view A-A of FIG. 18a.

DESCRIPTION OF THE INVENTION

Figure 1B:
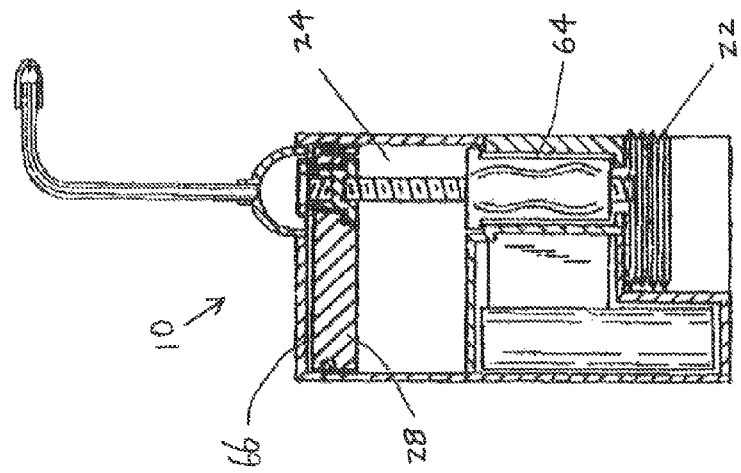
FIG. 1b is a front cross-section view of the implantable drug delivery pump device of FIG. 1a with the drug reservoir at empty state.

In the following descriptions, implantable drug delivery pump device and infusion pump are used interchangeably. First fluid and drug fluid are used interchangeably. Second fluid and filler fluid are used interchangeably. First chamber, drug chamber and drug reservoir are used interchangeably. Second chamber and filler fluid chamber are used interchangeably.

Further, the present invention relates to
1. An implantable drug delivery device comprising;
  a. housing walls,
  b. a first chamber supported by the housing walls having an outlet and containing a first fluid,
  c. a piston positioned inside said first chamber, being driven in forward and backward motions by a drive means, said piston moves the first fluid toward the outlet when being driven forward by a diver means,
  d. a second chamber having a collapsible wall containing a second fluid, said second fluid being separated from the first fluid by said piston, said collapsible wall collapses as the second fluid moves in with said piston in response to the reduced volume of the first fluid in the first chamber.
  e. a drive means for imparting motion of the piston.
2. An implantable drug delivery device of [1] wherein said housing walls and the collapsible wall are impermeable.
3. An implantable drug delivery device of [1] wherein said collapsible wall contracts as the second fluid moves in with said piston during the dispensing of the first fluid and said collapsible wall expands as the second fluid moves back with said piston when the first chamber is refilled with the first fluid.
4. An implantable drug delivery device comprising:
  a. housing walls,
  b. a first chamber supported by the housing walls having an outlet and containing a first fluid,
  c. a piston positioned inside said first chamber, being driven in forward and backward motions by a drive means, said piston moves the first fluid toward the outlet when being driven forward by the diver means,
  d. a catheter having a base end and a dispensing end, said base end being attached to the outlet,
  e. a positive-closing valve being attached to the dispensing end of said catheter, said positive-closing valve opens when the piston moves toward the outlet and closes when the piston moves away from the outlet,
  f. a septum being attached to the outlet, said septum being in flow communication with said first chamber and said catheter,
  g. a drive means for imparting motion of said piston.
5. An implantable drug delivery device of [4], wherein said positive-closing valve is a slit valve of a cap of elastomeric materials having a cross-slit cut at the apex of the cap forming a plurality of flexible flappers, said slit valve being at a closed position when no pumping pressure is exerted by the piston.
6. A process for preventing clogging of the positive-closing valve of an implantable drug delivery device of [4] wherein said drive means being controlled by a microprocessor, said microprocessor being programmed to move the piston forward a first distance for dispensing the first fluid and then to move the piston backward a second distance to ensure the closing of the self-sealing valve, said first distance being larger than the second distance by a value corresponding to a specified amount of the first fluid being dispensed.
7. A process for preventing clogging of the dispensing end of an implantable drug delivery device of [6] wherein said microprocessor provides repeated motions of opening and closing of the positive-closing valve by moving the piston forward and backward with a specified frequency and a specified amplitude that is incapable of dispensing the first fluid.
8. A process for refilling an implantable drug delivery device of [4] comprising the steps of:
  a. signaling a need to refill the first chamber by using the oscillation motion of said piston with a detectable amplitude and frequency,
  b. inserting the needle of a refill container containing the first fluid into said septum,
  c. retracting the piston away from the outlet by the drive means forcing the positive-closing valve to the closed position and resulting in withdrawing the refill fluid from the syringe into the first chamber.

9. An implantable drug delivery device of [4] including a second chamber which has a collapsible wall containing a second fluid. said second fluid being separated from the first fluid by said piston, said collapsible wall contracts as the second fluid moves in with said piston in response to the reduced volume of the first fluid in the first chamber.

10. An implantable drug delivery device comprising;
 a. housing walls,
 b. a first chamber supported by the housing walls having an outlet and containing a first fluid,
 c. a piston positioned inside said first chamber and being driven in forward and backward motions by a drive means, said piston moves the first fluid toward the outlet when being driven forward by a diver means,
 d. a septum, attached to the outlet, said septum being in flow communication with said first chamber and said catheter,
 e. a first magnet attached to said septum and a second magnet attached to said piston,
 f. a drive means for imparting motion to the piston,
 g. an IC control board supported by the housing walls, said IC control board includes a microprocessor, electrical circuits and is in communication with said drive means,
 h. an activation detector in communication with said first magnet and an electrical circuit in the IC control board that converts a change of magnetic field surrounding the first magnet into a voltage output.

11. An implantable drug deliver) device of [10] wherein said electrical circuit comprises Wheatstone bridge elements to convert the magnetic field into a voltage output for measuring the distance between the first magnet and the second magnet.

12. An implantable drug delivery device of [10] including a second chamber which has a collapsible wall containing a second fluid, said second fluid being separated from the first fluid by said piston, said collapsible wall contracts as the second fluid moves in with said piston in response to the reduced volume of the first fluid in the first chamber.

13. An implantable drug delivery device of [10] including a slit valve which is attached to the dispensing end of said catheter, said slit valve opens when the piston moves toward the outlet and closes when the piston moves away from the outlet.

14. An implantable drug delivery device of [10] including a second magnet which is attached to said piston and the distance between the first magnet and the second magnet being measurable by a magnet proximity sensor to determine the position of said piston in the first chamber.

15. An implantable drug delivery device of [10] in which flow gaps being created between the motor and the housing walls for the flow of the second fluid from the second chamber to the space behind the piston in the first chamber.

16. An implantable drug delivery device of [1], [4] or [10] wherein said drive means is a threaded rod and a motor imparting the rotation of the threaded rod, which causes forward and backward movements of the piston in the axial direction of the threaded rod corresponding to rotational directions of the motor.

17. An implantable drug delivery device of [16] wherein said motor is a piezoelectric motor or a stepper motor.

18. An implantable drug delivery device of [1] or [4] wherein said piston is made of ferrite material and said drive means comprising a permanent magnet positioned at the outlet end of the first chamber and a set of induction coils being supported by the housing walls, said induction coils magnetizing the piston to move in forward and backward directions depending on the polarity of the magnetic field induced by the induction coils responding to directions of electrical current imposed on the induction coils.

19. An implantable drug delivery device of [18] wherein said induction coils are controlled by an external controller using telemetry to monitor and change the operational parameters of said induction coils.

20. An implantable drug delivery device of [1] or [4] including an IC control board in electrical communication with the drive means.

21. An implantable drug delivery device of [20] including a battery in electrical communication with the IC control board.

22. An implantable drug delivery device of [18] wherein said piston moves toward the outlet position when the piston is magnetized with a polarity in the same polarity direction of the permanent magnet, and said piston moves away from the outlet position when said piston being magnetized with polarity in the opposite polarity direction of the permanent magnet.

23. An implantable drug delivery device of [17] wherein said piezoelectric motor has a threaded rod which is in free-to-rotate engagement with said piston, said piston having a non-circular cross-section undergoing linear movement without rotation.

24. An implantable drug delivery device of [17] wherein said stepper motor having a threaded shaft, said piston having non-circular cross-section and inner threads which are engaged with the threaded shaft, said piston moves in the axial direction of the threaded shaft when the stepper motor is activated.

25. A refill container for refilling an implantable drug delivery device comprising:
 a. a tubular housing with inner wall surface having first opening and second opening, said tubular housing containing a drug fluid,
 b. a needle being attached to the second opening and being in flow communication with the drug fluid,
 c. a disc situated inside said tubular housing being in slidable sealing fit with inner wall surface, said disc not accessible from outside the housing and being only movable following the flow direction toward the needle when the drug fluid being drawing out of the housing through the needle, said disc being exposing to ambient pressure through the first opening.

26. A refill container for refilling an implantable drug delivery device comprising:
 a. a collapsible pouch containing a drug fluid having flexible film wall fastened to a top plate having an exit opening, said film wall being collapsible when the drug fluid is drawn through the exit opening,
 b. a needle being attached to the exit opening of the top plate and being in flow communication with the drug fluid.

27. A refill container for refilling an implantable drug delivery device of [26] including an external tubular housing wall, separate from the collapsible pouch and forming a gap between the external housing wall and the flexible film wall of said collapsible pouch, said gap preventing the pouch from being collapsed by a deflection of the housing wall causing dispensing of drug fluid.

28. A refill container for refilling an implantable drug delivery device of [26] including an external tubular housing wall, whose deflection does not cause contraction of said collapsible pouch and forcing the dispensing of the drug fluid.

29. A refill container for refilling an implantable drug delivery device of [25], [26], [27] or [28] including an attached magnet surrounding the needle.

30. An implantable drug delivery device comprising;
a. housing walls,
b. an internal fluid chamber, containing a first fluid, is supported by housing walls and is divided into a first compartment and a second compartment by a wall having a one-way valve, the first compartment having an outlet and a piston and the second compartment having a follower which is in communication with the movement of the piston,
c. an external fluid chamber containing a second fluid is supported by housing walls and is enclosed partially by a collapsible wall, said second fluid being separated from the first fluid by the piston and the follower, said collapsible wall contracts as the second fluid moves in with said piston in respond to the reduced volume of the first fluid in the first chamber.
d. a drive means for imparting forward and backward movements of the piston, said forward movement for moving the first fluid toward the outlet and said backward movement for moving the first fluid away from the outlet.

31. An implantable drug delivery device of [30] wherein the forward movement of said piston causes the contraction of the collapsible wall and the backward movement of said piston causes the expansion of the collapsible wall.

32. An implantable drug delivery device of [30] wherein said walls of the internal chamber and the external chamber are impermeable to fluids present in an operating environment.

33. An implantable drug delivery device of [30] wherein said one-way valve closes when the piston moves toward the outlet and the one-way valve opens when the piston moves away from the outlet causing the first fluid to flow from the second compartment into the first compartment.

34. An implantable drug delivery device system comprising:
a. a refill container comprising housing walls, a reservoir containing first fluid and a needle,
b. an internal fluid chamber containing first fluid, said internal fluid chamber being divided by a wall having a one-way valve into a first compartment having a piston and a second compartment having a follower,
c. an outlet having opposing walls forming a flow channel in communication with said first compartment, said opposing walls can be forced to contact each other to block the flow of the first fluid by insertion of the needle of said refill container.
d. a drive means for imparting motion of the piston.

35. An implantable drug delivery device system of [34] having an external fluid chamber, containing a second fluid which is enclosed partially by collapsible walls, said second fluid being separated from said first fluid by the piston and the follower and fills the space left by the movements of the piston and the follower.

36. An implantable drug delivery pump device system of [34] having a septum attached with a first magnet for positioning the needle of the refill container for insertion into the septum.

37. An implantable drug delivery device system of [34] wherein said outlet is attached with a catheter having a positive closing valve mounted at the dispensing tip, said valve opens when the piston moves toward the outlet and closes when the piston moves away from the outlet.

38. An implantable drug delivery device system of [34] wherein the first fluid in said refill container is drawn into the internal fluid chamber by moving the piston away from the outlet.

39. An implantable drug delivery device system comprising:
a. a refill container comprising housing walls, a reservoir containing a refill fluid and a needle,
b. an internal chamber containing a first fluid and having an outlet and a piston, said outlet having opposing walls forming a flow channel for the flow of the first fluid,
c. a septum being attached to the outlet of said internal chamber, said septum having a plunger for being pushed by the needle of said refill container to block the flow channel of the outlet.

40. An implantable drug delivery device system comprising:
a. a refill container comprising housing walls, a reservoir containing a refill fluid and a needle,
b. an internal chamber containing a first fluid and having an outlet and a piston, said outlet having opposing walls forming a flow channel for the flow of the first fluid,
c. a drive means for imparting forward and backward movements of the piston, said forward movement for moving the first fluid toward the outlet and said backward movement for moving the first fluid away from the outlet.
d. a contact switch in electrical communication with said drive means, said contact switch being activated by the insertion of the needle of said refill container activating the movement of the piston.

41. An implantable drug delivery device system of [40] wherein said contact switch having opposing electrode plates with each electrode plate being attached to said opposing walls of said outlet, and said opposing walls can be forced to contact each other thereby blocking the flow of the first fluid through the outlet, and said movement of the piston causing the flow of the first fluid from the refill container to the internal fluid chamber.

42. An implantable drug delivery device system of [40] wherein said contact switch being formed by a stationary electrode plate and a movable electrode plate, said movable electrode plate being attached to a plunger which is spring loaded against a partition wall dividing a piston chamber and a reservoir chamber.

43. An implantable drug delivery device system of [40] having an external fluid chamber containing a second fluid that is enclosed partially by collapsible walls, said second fluid being separated from said first fluid by the piston and fills the space left by the movement of the piston.

44. An implantable drug delivery device system of [40] having a septum attached with a first magnet for positioning the refill container for insertion into the septum.

45. An implantable drug delivery device system of [40] wherein the first fluid in said refill container being drawn into the internal fluid chamber by moving the piston away from the outlet.

46. An implantable drug delivery device of [30], [34] or [40] wherein said drive means is a threaded rod and a motor imparting the rotation of the threaded rod, which causes forward and backward movements of the piston in the axial direction of the threaded rod corresponding to the rotational direction of the motor.

47. An implantable drug delivery device of [30], [34] or [40] wherein said motor is a piezoelectric motor comprising a threaded rod and piezoelectric plates with one end forming a threaded-nut configuration and, said threaded rod rotates when said piezoelectric plates being in piezoelectric vibration.

48. An implantable drug delivery device of [30], [34] or [40] wherein said internal fluid chamber having two parallel sidewalls and one of said sidewalls is attached with said external fluid chamber having said collapsible walls containing the second fluid, which fills the space left by the movements of the piston and the follower.

49. A process of ensuring positive-closing of the slit valve of an implantable drug delivery device of [30], [34] or [40] wherein said drive means is controlled by a microprocessor, said microprocessor being programmed to move the piston forward for a first distance to dispense the first fluid and then to move the piston backward for a second distance to ensure the closing of the self-sealing valve, said first distance being larger than the second distance by a value corresponding to a specified amount of the first fluid being dispensed.

50. A process of refilling an implantable drug delivery device of [30], [34] or [40] comprising steps of:
   a. inserting a refill container containing first fluid into said septum,
   b. retracting the piston away from the outlet by the drive means resulting in withdrawing the refill fluid from the refill container into the first chamber.

51. A process for refilling an implantable drug delivery device of [50] wherein the refill container is of the passive type having no plunger for manually injecting first fluid into said first chamber.

52. A process of refilling an implantable drug delivery device of [50] or [51] including a step of signaling a need to refill the first chamber by using the reciprocating motion of said piston with a detectable amplitude and frequency, 53. A process of verifying the movement of a follower in a drug chamber of an implantable drug delivery device of [36] and [44] including a second magnet being attached to the follower and measuring the distance between the second magnet and the first ring magnet at the septum by a magnet proximity sensor.

54. An implantable drug delivery device comprising a drug fluid chamber, a reciprocating piston and a battery for powering the reciprocating motion of the piston, said battery having a batterylow circuit and said piston being programmed to perform the reciprocating motion at detectable amplitude and frequency as a notification for battery recharge or replacement upon receiving a battery low signal from the battery-low circuit.

55. An implantable drug delivery device of [54] wherein said piston is retracted for a predetermined distance and driven for said reciprocating motion without dispensing the drug fluid.

56. An implantable drug delivery device of [54] or [55] having a positive-closing valve attached to said drug fluid chamber, said positive-closing valve remaining at closed position when the piston is retracted for said distance and performing said reciprocating motion.

57. An implantable dual drug delivery device comprising:
   a. a first drug chamber containing a first drug fluid and having a first outlet, a septum and a first piston,
   b. a first magnet having a first polarity attached to the septum of said first drug chamber,
   c. a second drug chamber containing a second drug fluid and having a second outlet, a septum and a second piston,
   d. a second magnet having a second polarity attached to the septum of said second drug chamber, the second polarity being opposite to the first magnet polarity, 58. An implantable dual drug delivery device of [57] including an external chamber, said external chamber containing a third fluid enclosed partially by a collapsible soft layer, said third fluid being separated from the first drug fluid and the second drug fluid by the first piston and the second piston.

59. An implantable dual drug delivery device of [57] wherein said first and second magnets are ring magnets.

60. An implantable dual drug delivery device of [57] wherein the first piston is driven by a first motor and the second piston is driven by a second motor.

61. An implantable dual drug delivery device comprising:
   a. a first drug chamber containing first drug fluid, said first drug fluid chamber being divided by a wall having a one-way valve into a first compartment having a piston and a second compartment having a follower,
   b. a second drug chamber containing second drug fluid, said second drug fluid chamber being divided by a wall having a one-way valve into a first compartment having a piston and a second compartment having a follower,
   c. a first catheter and a first septum being attached to said first drug chamber, said first catheter having opposing walls forming a flow channel in communication with the first drug compartment, said opposing walls can be forced to contact each other to block the flow of the first drug fluid,
   d. a second catheter and a second septum being attached to said second drug chamber, said second catheter having opposing walls forming a flow channel in communication with the second drug compartment, said opposing walls can be forced to contact each other to block the flow of the second drug fluid,
   e. a first magnet having a first polarity being attached to the septum of said first drug chamber,
   f. a second magnet having a second polarity being attached to the septum of said second drug chamber, the second polarity being opposite to the first polarity.

62. An implantable dual drug delivery device of [61] having an external chamber containing a third fluid, enclosed partially by a collapsible soft layer, said third fluid being separated from the first drug fluid and the second drug fluid by the pistons and the followers.

63. A refill container for refilling an implantable dual drug delivery device comprising:
   a. a tubular housing wall containing a drug fluid, said tubular housing having a valve chamber with a top opening end and a reservoir chamber with a bottom enclosed end,
   b. a needle attached to the top opening end of the valve chamber,
   c. an orifice plate being positioned separating the valve chamber and the reservoir chamber, said orifice plate having an orifice at the center for passing the drug fluid from the reservoir chamber to the valve chamber.
   d. a magnet valve having a polarity and being movably attached to the valve chamber, said magnet valve blocks the opening of the orifice plate when moved in contact with the orifice plate
   and allows for the flow from the reservoir chamber to the needle when said magnet valve is moved away from the orifice plate.

64. A refill container for refilling an implantable dual drug delivery device of [63] wherein said magnet valve having a platform including a central solid area and slot openings, said central solid area capable of blocking the orifice of the orifice plate and said slot openings are blocked by said orifice plate when said magnet valve is moved in contact with the orifice plate.

65. An implantable dual drug delivery device and refill system comprising:
   a. a first refill container containing a first drug fluid having a ring magnet valve with a first polarity,
   b. a second refill container containing a second drug fluid having a ring magnet valve with a second polarity, c. a first drug chamber containing a first drug fluid and having an outlet, a septum and a first piston, said septum being attached with a first magnet with first polarity attracting the ring magnet valve of the first refill container, d. a second drug chamber containing a second drug fluid and having an outlet, a septum and a second piston, said septum being attached with a second magnet with second polarity attracting the magnet valve of the second refill container, said second polarity being opposite to the first polarity of said first refill container.

66. An implantable dual drug delivery device and refill system of [65] wherein the first ring magnet of said first drug chamber repels the magnet valve of the second refill container thereby blocking the drug flow inside the second refill container.

67. An implantable dual drug delivery device and refill system of [57] or [65] wherein the first piston is driven by a first motor and the second piston is driven by a second motor.

68. An implantable dual drug delivery device of [67] including an external chamber, said external chamber containing a third fluid enclosed partially by a collapsible soft layer, said third fluid being separated from the first drug fluid and the second drug fluid by the first piston and the second piston.

69. An implantable dual drug delivery device and refill system of [57] or [67] wherein the outlet of each drug chamber is attached with a catheter with a slit valve mounted at the dispensing tip, said slit valve opens when the piston in each drug chamber moves toward the outlet and closes when the piston moves away from the outlet.

70. An implantable dual drug delivery device and refill system of [57] or [67] wherein the drug fluid in each refill container is drawn into a matched drug chamber by moving the piston away from the outlet.

71. An implantable dual drug delivery device and refill system of [69] wherein the outlet of each drug chamber having opposing walls forming a flow channel in communication with the drug fluid in the chamber, said opposing walls can be forced to contact each other to block the flow into the catheter when activated by the needle of a refill container.

72. An implantable dual drug delivery device and refill system of [61], [65] or [69] wherein each outlet has a contact switch, said contact switch having opposing electrode plates with each electrode plate being attached to said opposing walls of said outlet walls, and said opposing walls can be forced to contact each other to block the flow into the catheter and activate the movement of the piston when activated by the needle of said refill container causing the drug fluid to be drawn from the refill container to the drug chamber.

73. An implantable dual drug delivery device of [57], [61] or [67] including a motor driver, a battery and an IC control board with control software, said motor driver controls the movements of the first and the second pistons through the control software of the IC control board and powered by the battery.

74. An implantable dual drug delivery device of [57], [61] or [67] wherein each motor is a piezoelectric motor comprising a threaded rod and piezoelectric plates with one end forming a threaded-nut configuration and, said threaded rod rotates when said piezoelectric plates being in ultrasonic vibration.

75. An implantable dual drug delivery device of [57], [61] or [65] wherein the two drug chambers are oriented in the same direction.

76. An implantable dual drug delivery pump device of [57], [61] or [65] wherein the two drug chambers are oriented in opposite directions.

77. A process of ensuring positive closing of the slit valve of the implantable dual drug delivery device of [73] wherein said motor driver with software control moves each piston forward for a first distance for dispensing the drug fluid and then to move the piston backward for a second distance to ensure the closing of the slit valve, said first distance being larger than the second distance by a value corresponding to a specified amount of the drug fluid being dispensed.

78. A process to verify the movement of a follower in a drug chamber of an implantable dual drug delivery pump device of [61] including a follower magnet being attached to the follower and measuring the distance between the follower magnet and the septum magnet by a magnet proximity sensor for determining the position of said follower in the drug chamber.

Figure 1A:
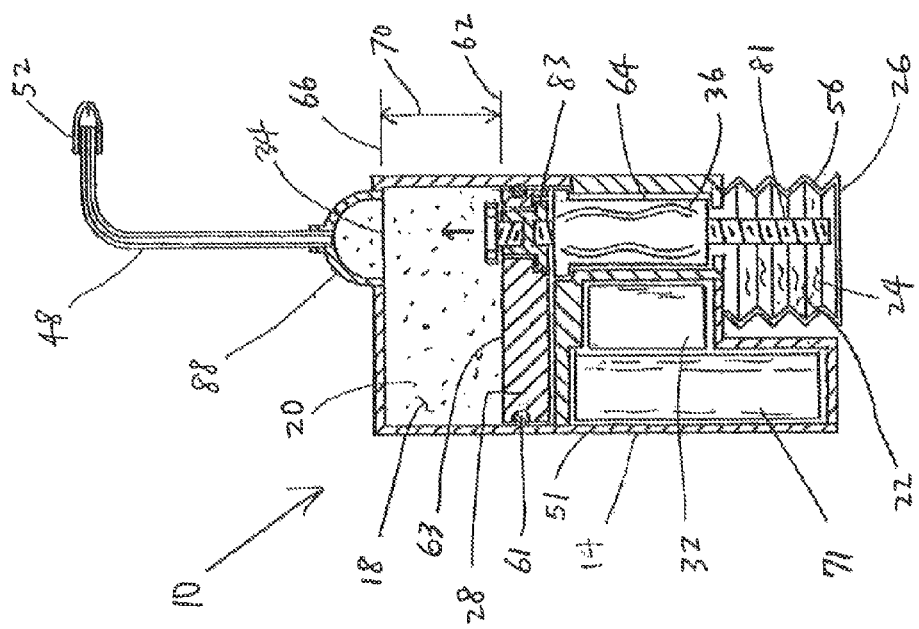
FIG. 1a is a front cross-section view of an implantable drug delivery pump device using a piezoelectric motor with a drug reservoir at full state.

79. An implantable dual drug delivery device of [61] or [62] wherein said first magnet and second magnet are ring magnets Single-Drug-Chamber Device Configuration As shown in FIG. 1a an implantable drug delivery pump device 10 of the present invention comprises a pump housing having walls 14 including two fluid chambers separated by a piston with the first chamber 18 as a reservoir containing first or drug fluid 20, and the second chamber 22 containing second or filler fluid 24 which is enclosed partially by a collapsible wall 26. Second fluid 24 is used as a filler fluid which is inert to the drug fluid and body tissues. Piston 28 prevents fluid communication between first chamber 18 and second chamber 22. The piston is driven by a drive means, powered by battery 71, for infusing the first fluid through outlet 34 and reducing the volume of the first fluid in the first chamber with the vacated space filled in by the filler fluid, which is accompanied by the collapsing of the collapsible wall. The fill-in motion of the filler fluid prevents creation of a vacuum that, if allowed to exist, can negatively impact the movement of the piston. In this configuration the walls of the first chamber containing the drug fluid are rigid with internal contact surfaces not hindering the movement of the piston. In addition, walls 51 and 56 of the first and the second chambers 18 and 22, respectively, are impermeable to external fluids present in a body tissue environment. In particular, wall 51 of first chamber 18 is made of a drug-compatible, implantable material of sufficient rigidity without deformation so as not to hinder the movement of piston inside the reservoir chamber. For example, the wall material of the first chamber may be constructed from a metal, such as titanium, nickel titanium, stainless steel, anodized aluminum, or tantalum, or a plastic, such as polyethylene, nylon, or polyurethane. However, wall 56 of second chamber 22 is made of flexible material such as silicone, polyurethane, which allows the wall to expand or collapse as fluid is added or withdrawn from the first chamber into the second chamber. A bellow configuration 26 is illustrated in FIG. 1a in representing the collapsible nature of the second chamber to enable the movement of the filler fluid in filling in the space reduced or vacated by the dispensing of the first fluid. Furthermore, a catheter 48 is attached to outlet 34 of first chamber 18 in flow communication with the first fluid 20. The wall of the first chamber includes a filling septum 44, which enables a physician to inject drugs into the drug chamber. An outlet valve in a form of slit valve 52 is attached at dispensing end of the catheter. A normally closed slit valve prevents backflow of fluids from the outside environment into the device. The slit valve is forced to open by the forward movement 60 of the piston exerting pumping pressure allowing the drug to be dosed from the reservoir to the treatment site. The implantable pump device is implanted into a body cavity, and the catheter can be led to an appropriate tissue or space for dispensing the drug.

Piston Motion

The first fluid 20 is pushed by the forward movement 60 of piston 28. The piston performs forward and backward motions under the control of a motor driver, which is mounted in IC control board 32 and is preprogrammed. The perimeter surface of the piston is in sliding-sealing fit, represented by O-ring 61, with the inner wall surface of the first chamber. During the forward motion of the piston the slit valve at the end of the catheter is forced to open to dispense the therapeutic liquid. As a result, the second fluid from the second chamber enters the first chamber through the flow gaps 64 to fill in the space behind the piston head left by the movement of the piston. The sliding-sealing fit or the wiping contact of the piston perimeter surface with the inner wall of the first chamber ensures no residual trace of drug fluid, i.e. the first fluid, left behind the piston in contact with the filler fluid, i.e. the second fluid, and similarly no residual trace of the filler fluid left on the opposite side of the piston will be in contact with the drug fluid.

The filling motion of the filler fluid into the first chamber reduces the volume in the second chamber, therefore, causes the bellow wall or the collapsible wall to close in. Conversely, a backward or retracting motion of the piston creates a negative pressure drop that causes the slit valve to close. With the slit valve closed, further retraction of the piston is hindered due to vacuum pressure created inside the first chamber. For a given drug dosage at each infusion event, the number of forward pulses and the immediate number of backward pulses can be predetermined for the device to provide the desired net amount of drug dispensed at the event through the slit valve. In each infusion event the number of forward pulses or forward distance is greater than the number of backward pulses or backward distance which results in the desirable amount of drug dosage exiting from the one-way slit valve at the dispensing end of the catheter. Moreover, the capability of the reciprocating motion of the piston can be utilized for refilling notification as will be described in later sections.

Slit Valve

In a preferred embodiment a positive-closing slit valve 52 is a molded dome-shaped cap of elastomeric materials having a cross-slit cut forming a plurality of flexible flappers. In a preferred embodiment a slit valve used for the implantable drug delivery pump device of this invention is of a biocompatible silicone material. The slit valve has a tubular wall base and four flappers. Each flapper is a curved triangular valve segment extending from the tubular wall base with the tip of each valve segment intercepting at the center, i.e. at the apex of the slit valve opening when the slit valve is at the closed position. Each valve segment can be bent like a cantilever beam under the pressure of a dispensing flow. The slit length, wall thickness and the elastic modulus of the valve material are designed to ensure self-closing of the slit valve by the resiliency and the vacuum force at the absence of pumping pressure. With the use of a slit-valve, it is not necessary to use an outlet check valve to prevent backflow.

The valve opens under positive piston pressure to dispense first fluid and the cross-slit valve closes under negative piston pressure when the piston is moved away from the outlet by the drive means. In practice, infusion of the drug is achieved in pulsed steps at predetermined time intervals. In each repeated infusion events, the therapeutic fluid is incrementally dispensed and the collapsible wall or the bellow wall is moving forward in each cycle. This process continues until the first chamber 18, i.e. the drug reservoir, is depleted of the first or the drug fluid. As shown in FIG. 1*b*, in the drug-spent or reservoir empty state the space 72 behind the piston in first chamber 18 is full of the filler fluid 24. A dispensing phase starts from the piston home position 62, which is defined as the piston top surface 63 in contact with the first fluid being at the lower travel limit of the piston, and ends when the piston's top surface is at the upper travel limit 66.

Refilling

Figure 2B:
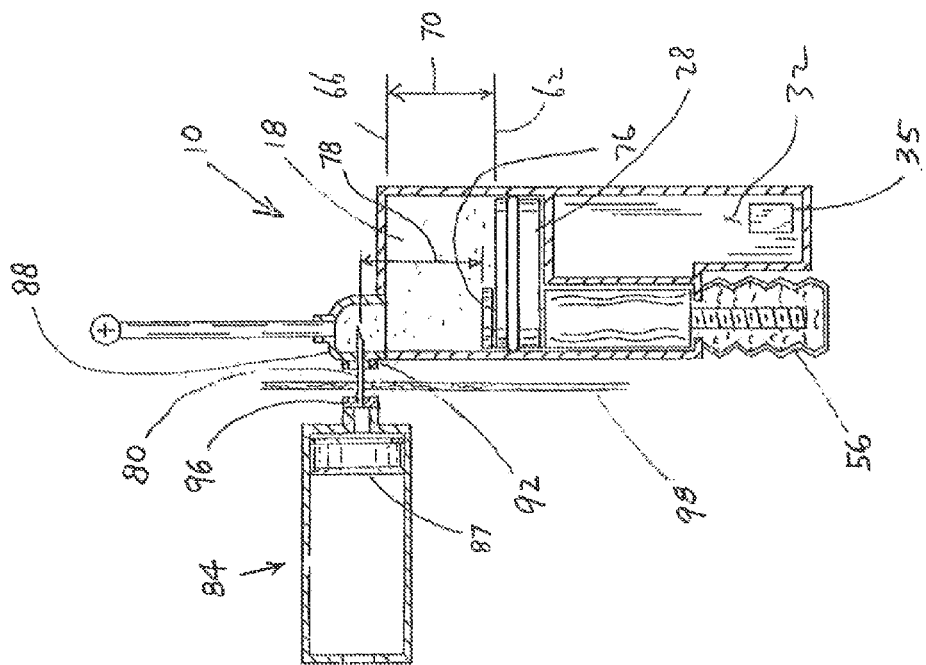
Figure 2A:
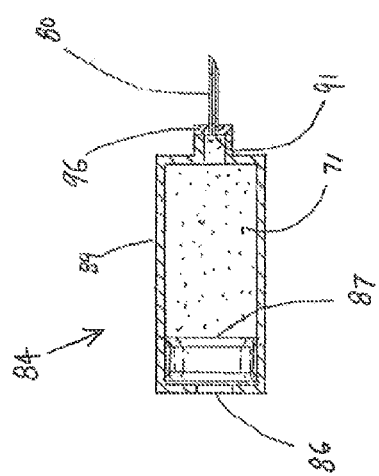
FIG. 2a is a side cross-section view of a refill container of the present invention using a slidable disc.

Referring to FIGS. 2*a* and 2*b*, refilling of the drug chamber can be accomplished by inserting a needle 80 of a refill container 84 into a septum 88 of the drug delivery pump device 10. In one embodiment refill container 84 having drug fluid 71 comprises a tubular housing wall 89 having a first opening 86 and second opening 91, disc 87, magnet 96 and needle 80. Disc 87 is in movable fit with the inner wall of housing 89 and the opening 89 maintains the disc at ambient pressure. To prevent external actuation, disc 87 is not accessible manually from outside housing 89 and it is only movable when following the flow direction toward the needle when the drug fluid is drawing out of the housing through the needle. Magnet 96 is preferably a ring magnet. Both magnet 96 and needle 80 are attached to housing wall 89 with the needle being attached to second opening 91 for the passage of drug fluid 71. FIG. 2*a* shows refill container 84 being full of refill drug fluid 71. Magnet 96 surrounds the needle to guide the positioning of the needle when inserting to septum 88 which is attached with magnet 92. In another embodiment, the refill container for an implantable drug delivery device of this present invention uses a collapsible pouch having a thin flexible wall for containing a drug fluid. No movable disc is required. FIG. 2*c* shows a refill container assembly 184 using a rigid outer housing wall 189 to shield the collapsible pouch 188. The thin flexible wall 187 of collapsible pouch 188 is fastened to a top plate 190 forming an enclosure containing drug fluid 171. The top plate has exit opening 191 as a flow path for the drug fluid drawn out of the collapsible pouch. Needle 180 is attached to the exit opening 191 by threaded engagement between the needle and the housing. Alternatively, the needle may be directly threaded onto the top plate 190 of the pouch. FIGS. 2*c* and 2*d* illustrate the assembly housing comprising two foldable halves 150 and 152 for ease of inserting the collapsible pouch and mounting the needle. With this foldable configuration magnet ring 196, which surrounds the needle, may be divided into two halves with each attached to a half of the housing wall. To prevent external ambient pressure from contracting the collapsible pouch and forcing out the drug fluid, the external housing wall 189 is designed to be rigid and not deformable to contact on the collapsible pouch. Optionally, gap 154 exits between the housing wall 189, which is of tubular form, and the collapsible pouch 188 such that the housing wall does not deform preventing contraction of the collapsible pouch which would have resulted in inadvertent dispensing of the drug fluid. FIG. 2*d* shows that collapsible pouch 188 contracts only when drug fluid 171 is drawn out from needle 180 under a vacuum 195, which occurs during the refilling process when the needle is inserted into the septum of drug delivery device 10. This passive type of refill container which depends on insertion into the septum of a drug delivery device for withdrawing the drug fluid is a safety feature to prevent inadvertent injection of the drug fluid into body tissues if the device is not properly connected to the septum.

For the insertion of a refill container needle, magnet 92 attached to septum 88 is preferably a raised ring for guiding the positioning of the needle through the skin 98. The raised ring 92 may be in a form of ring magnet of a polarity that attracts a ring magnet 96 of opposite polarity mounted on the needle 80 of the refill container 84. The attraction between the two magnets 92 and 96 across the skin can facilitate positioning and stabilizing the needle 80 during injection. PDMS, which is Polydimethylsiloxane a silicon-based organic polymer material, may be selected as a septum material for its flexibility and ability to reseal itself after repeated punctures via a needle attached to the refill container.

As a reverse of the dispensing function, the retraction or backward movement of the piston draws the refill fluid from the refill container into the first chamber. Continuous retracting motion of the piston can draw in the refill fluid to fill the first chamber while the catheter entrance remains closed by the negative pressure drop. FIG. 2 shows completion of a refilling process and the piston is at its home position 62. The refill container is of the "passive type" and does not have a plunger thereby minimizing the risk of inadvertently injecting drug into a body cavity. Refilling from the refill container is possible only when the needle is inserted into the septum and the retracting action of the piston draws in the drug solution by vacuum, a safety feature of this invention as described. As the piston is retracted the collapsible wall 56 expands corresponding to the volume of the refill-fluid being drawn into the first chamber.

Activation Detector

To ensure a readiness for refilling, the refilling process can start only when an activation detector is activated. The permanent magnet 92 mounted on septum 88 as shown in FIG. 2 is attached with an internal magnet proximity sensor (not shown) to function as an activation detector for triggering the controller and the motor driver in control board 32. The use of a magnet proximity sensor using Hall Effect for tuning the operational gradient of the magnetic field normal to the face of the detector is known in the art. Commercially magneto-resistive sensors of the Honeywell Company may be used as an activation detector. These sensors have a high sensitivity with conventional magnets like AlNiCo and ceramic materials and their Wheatstone bridge elements convert the magnetic field direction into a voltage output. Optionally, a Reed Sensor of Cherry Corporation may be used as a magnetically activated switch. The internal magnet proximity sensor (not shown) is in electrical communication with the motor driver and the microprocessor in the IC board of the pump device. To save space in the septum area the Hall Effect circuit 35 of the magnet proximity sensor is integrated in the IC board 32. When a specified starter-magnet, for activating the pump device, is placed on top of the magnet ring 92 of the pump device 10 across the skin 98, the activation detector (not shown) detects the change of the magnetic field surrounding the magnet ring 92 and the circuit of the proximity sensor converts the change of magnetic field into a voltage output. The activation detector triggers the controller and the motor driver to start the dispensing function of the pump device with forward motion of the piston. Similarly, when starting a refilling process, a specified refill-magnet is placed on top of the magnet ring 92 across the skin. The refill-magnet is preferably being magnet 96 attached to the needle or part of the refill container. Thus the approaching and docking of a refill container needle can cause the activation detector to activate the pump device with backward motion of the piston for refilling the drug chamber.

Notification Mode

For a given implantable drug delivery device and a given infusion profile for a patient, the refill interval is known and, therefore, the time to refill can be planned. However, if refilling does not occur at the appropriate time, a notification signal can be sent by the implantable drug delivery device of this invention. The notification feature utilizes the reciprocating motion of the piston. The motor driver can be programmed to perform a reciprocating motion of the piston at the end of a dispensing cycle to signal for refilling. The amplitude and the frequency of the reciprocating motion are pre-tested for generating a vibration of the pump device which does not cause any harm but is detectable by the patient. As a reminder to the patient to have the device refilled the reciprocating motion may be repeated to signal at a prescribed interval, which is to be determined (TBD) for a patient using the device. For instance the notification mode or the oscillation of the piston may be programmed to repeat at every 12 or 24 hours, depending on the drug and other factors such as coinciding with convenient day time schedules for taking action.

Verification

Additionally, there are a number of factors that may cause performance failures of an implanted device. These factors include the malfunction of electronics, hesitation in piston movement, voids in the drug reservoir and possible clogging at the dispensing opening. Therefore, an independent verification of the performance of an implant device is essential to ensure the reliable and predictable performance for the device. For verification of the pump performance of the present invention the position of the piston or a residual amount of dispensing material in the first chamber can be measured externally. As shown in FIG. 2, piston 28 is fitted with a magnet 76 and the displacement of the magnet mounted on top of the piston can be determined by measuring the distance 70 between the piston magnet 76 and the septum magnet 92, which is positioned at the center of the septum. The distance between the two magnets can be measured by an external magnetic proximity sensor positioned across the skin. A magnetic proximity sensor can be a commercially available Honeywell HMC1501 or HMC1512 magneto-resistive sensor. These sensors feature Wheatstone bridge elements to convert the magnetic field into a voltage output. The HMC sensors provide reliable performance in accuracy and resolution. This pump performance verification method is more convenient than a method of software interrogation of the number of pulses recorded in the microprocessor chip used for controlling the piston motion for dispensing drug dosages.

Piezoelectric Motor

A drive means of an implantable drug delivery pump device of the present invention can be a threaded rod 81 driven by motor 36 as illustrated in FIG. 1a. The rotation of the threaded rod 81 causes forward and backward movements of piston 28 corresponding to the rotational direction of the motor. As noted previously the mounting of motor 36 creates flow gaps 64 to allow second fluid 24 enter the first chamber behind the piston separating from the first fluid 20. The second fluid is partially enclosed by the collapsible wall represented by the bellow 26.

Preferably, a motor is a piezoelectric motor 36 as illustrated in FIG. 1a comprising a threaded rod and piezoelectric plates with one end forming a threaded-nut configuration (not shown). The vibration of the piezoelectric plates can cause the threaded rod to rotate. The threaded rod 56 is in free-to-rotate engagement with the piston 28. Generally the piston may have a non-circular cross-section undergoing linear movement without rotation. The conversion of the rotational motion of threaded rod 81 to a linear motion of the piston is achieved by using a rotational sleeve 83 and rotational retainer 85. The assembly contains a means for subjecting the threaded nut to ultrasonic vibration causing the threaded shaft to simultaneously rotate and translate in the axial direction. A cylinder supports a threaded nut with a first bending mode resonant frequency in the ultrasonic range. The cylinder and nut are excited at this resonant frequency by transducers that cause the nut to orbit at the end of the cylinder. The transducers may be piezoelectric, electromagnetic or any device that can stimulate the resonant vibration. A detailed description of a piezoelectric motor is given in U.S. Pat. No. 6,940,209 by Henderson.

Stepper Motor

Figure 3:
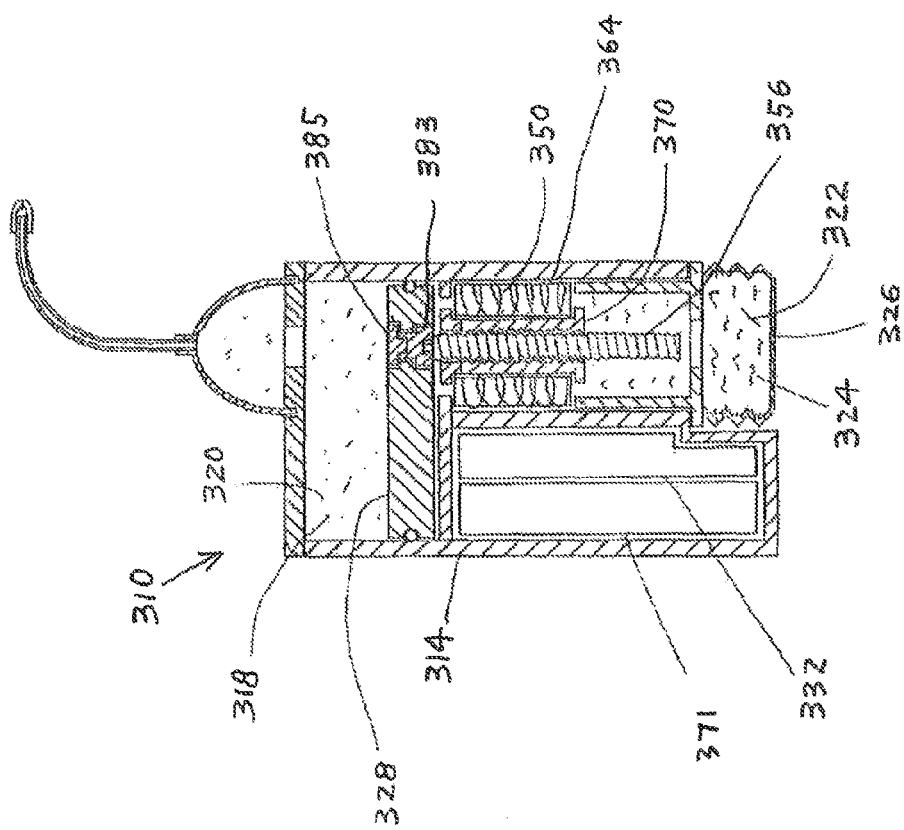
FIG. 3 is a front cross-section view of an implantable drug delivery pump device using a stepper motor.

Alternatively as shown in FIG. 3, a piston in an implantable drug delivery pump device of the present invention can be driven by a stepper motor which comprises coils 350 and a threaded shaft 356. For description purposes, FIG. 3 shows an implantable drug delivery pump device 310 of the present invention comprising a pump housing having walls 314 including two fluid chambers separated by piston 328 with the first chamber 318 as a reservoir containing first or drug fluid 320, and the second chamber 322 containing second or filler fluid 324 which is enclosed partially by a collapsible wall 326. Flow gaps behind the piston head allow the second fluid to enter the first chamber preventing any vacuum as the piston moves. Piston 328 is driven by stepper motor 370, which is mounted with thread shaft 356.

Generally piston 328 has a non-circular cross-section and is attached with a free-to-rotate sleeve 383 and rotational retainer 385 to convert the rotational motion of the thread shaft to a linear motion of the piston. The displacement of the piston is proportional to the number of pulses given to the motor coils. The use of a stepper motor is particularly advantageous because the signals applied to its coils are directly related to the displacement of the piston without requiring shaft encoders or sensors. The stepper motor is controlled by the control board 332 which includes an oscillator and a microprocessor and powered by battery 371. Optionally the oscillator may also be in communication with an external controller by passive telemetry for monitoring and correction of the performance of the device.

Induction Coils

Another alternative for driving a piston involves using induction coils. A piston made of electromagnetic or ferrite material can be magnetized by induction coils when an electric current passes through the coil. For description purpose, FIG. 4a shows an implantable drug delivery pump device 410 of the present invention that comprises a pump housing having walls 414 including two fluid chambers separated by piston 428 with the first chamber 418 as a reservoir containing first or drug fluid 420, and the second chamber 422 containing second or filler fluid 424 which is enclosed partially by a collapsible wall 426. Flow opening 464 allows second fluid 424 to enter first chamber behind piston 428 separating from the first fluid. Piston 428 is driven by electrical coils 430 mounted in the annular gap of a cylindrical housing 414 and in a sliding-and-sealing fit with the inner surface of the housing wall 444. A drive means for a piston of an implantable drug delivery pump device of the present invention comprises a permanent magnet 458 positioned at the outlet end 434 of the first chamber 418 and induction coils 430 being supported by the housing wall 444. The induction coils magnetize the piston to move in forward and backward directions depending on the polarity of the magnetic field induced by the induction coils in responding to the direction of the electrical current imposed on the induction coils. Piston 428 moves toward the outlet position 434 when the piston is magnetized with a polarity in the same polarity direction as the permanent magnet 458, and the piston moves away from the outlet position when the piston is magnetized with a polarity in the opposite polarity direction to that of the permanent magnet. For an implantable drug delivery pump device 410 of the present invention using induction coils for driving a piston, the dispensing cycle, the refilling process is similar to what has been described previously. Infusion pump 410 may also include the aforementioned activation detector and verification features. Furthermore, the control of the pump device 410 is accomplished by an external device containing induction coils 460, which is positioned across the skin 408 opposite to the induction coils 430 of the pump device. FIG. 4b shows a pump device 410 at the empty state with piston 428 reaching the maximum of travel distance near the outlet opening 434 and the wall of bellow 426 collapsing due to the flow of second fluid 424 filling in the space behind the piston. Also shown in FIG. 4b is needle 409 of the refilling syringe 470 inserted in septum 406 to start a refilling process, which is controlled by an external controller (not shown) represented by induction coils 460.

The timing and frequency of the current pulses applied to the coils can be controlled by an external controller (not shown). Use of an external controller for changing the operational parameter set is well known in the art, such as described in US Patent Application 20080108862 by Jordan; Alain et al. All the activity of the pump is recorded in a memory and a patient can access the data and change the pump parameters by radio frequency (RF) communication with an external control unit. An alternative method without using an RF emitter in an implanted device as "passive telemetry by absorption modulation" by P. A. Neukomm is described in CH 676164, WO 89111701, EP 0377695 and in the article Passive Wireless Actuator Control and Sensor Signal Transmission, Sensors and Actuators, A21-A23 (1990), 258-262.

Software Control Elements

The control software in the microprocessor controller of the present invention is programmed to provide Dispensing Mode, Refilling Mode, Notification Mode and Verification-Calibration Mode. In the Dispensing Mode, the microprocessor commands to provide pulses of different durations to control the dispensing rates depending on a prescribed dosage profile, which are converted into a set of operational parameters for the operation of the motor driver. At each dispensing command, after the pre-determined forward pulses, a pre-determined number of backward pulses follow to ensure positive-closing of the slit valve. The required number of backward pulses for closing the slit valve is less than the number of forward pulsed for dispensing such that the desirable amount of drug dosage is dispensed. The schedules and timings of the controller action are based on inputs from an IC oscillator timer built in the IC board of the pump device. The IC circuit for an oscillator timer is well known in the art. With an external controller, the operational parameter set (OPS) in the implant pump of the present invention can be changed as needed. In addition a memory chip in the pump device records the history of forward and backward pulses. An algorithm is provided in the control program to monitor the current amount of drug remaining in the reservoir such that the timing for refilling the reservoir is determined. The maximum travel distance of the piston between the reservoir full and reservoir empty is converted into the maximum number of dispensing pulses, which is pre-programmed with a safety factor in the controller. When the maximum number of dispensing pulses is reached, no further forward movement of the piston is commanded.

In the Refilling Mode, the needle of a refill container is inserted into the septum and the content is drawn into the first chamber by the retraction of the pump piston. The refill container is of a passive type without having an active plunger for external manual injection, therefore, preventing accidental administration of drug into wrong body tissues. The docking of the needle with the approach of the refill-magnet on the refill container initiates the refilling mode, and the controller microprocessor of the pump device of the present invention commands the motor driver to start the retraction motion of the piston. The motor may be programmed to run at a higher retraction speed at the refilling mode than the speed at the dispensing mode. The duration of the refilling mode is preprogrammed according to the maximum traveling distance of the piston for complete filling of the reservoir.

The Notification Mode can be programmed for repeated vibration of the pump device to alert the patient to take action to have the pump device refilled. The piston oscillation is initiated at the end of the Dispensing Mode, therefore, no additional drug is dispensed from the slit valve at the Notification Mode. The reciprocation of the piston is operated at detectable amplitude and frequency for a short duration such as a few seconds. The objective is to create vibrations which do not cause any harm or discomfort to the patient but are adequate to alert the patient to take action. At the Notification Mode, the command for the oscillation motion of the piston is repeated over a time interval.

In the Verification-Calibration Mode, the control program of the infusion pump of the present invention uses the input of a magnetic proximity sensor to measure the distance between the two magnets in the implant pump. The measured distance between the two magnets is converted and compared to the number of pulses for dispensing as recorded in the memory chip. Any discrepancy will be re-adjusted and re-calibrated in the operational parameter set to achieve a correct dispensing profile for continuous usage of the pump device. Such a verification-calibration mode may be integrated with the refilling mode such that the verification-calibration mode is conducted prior to the refilling action.

Figure 5:
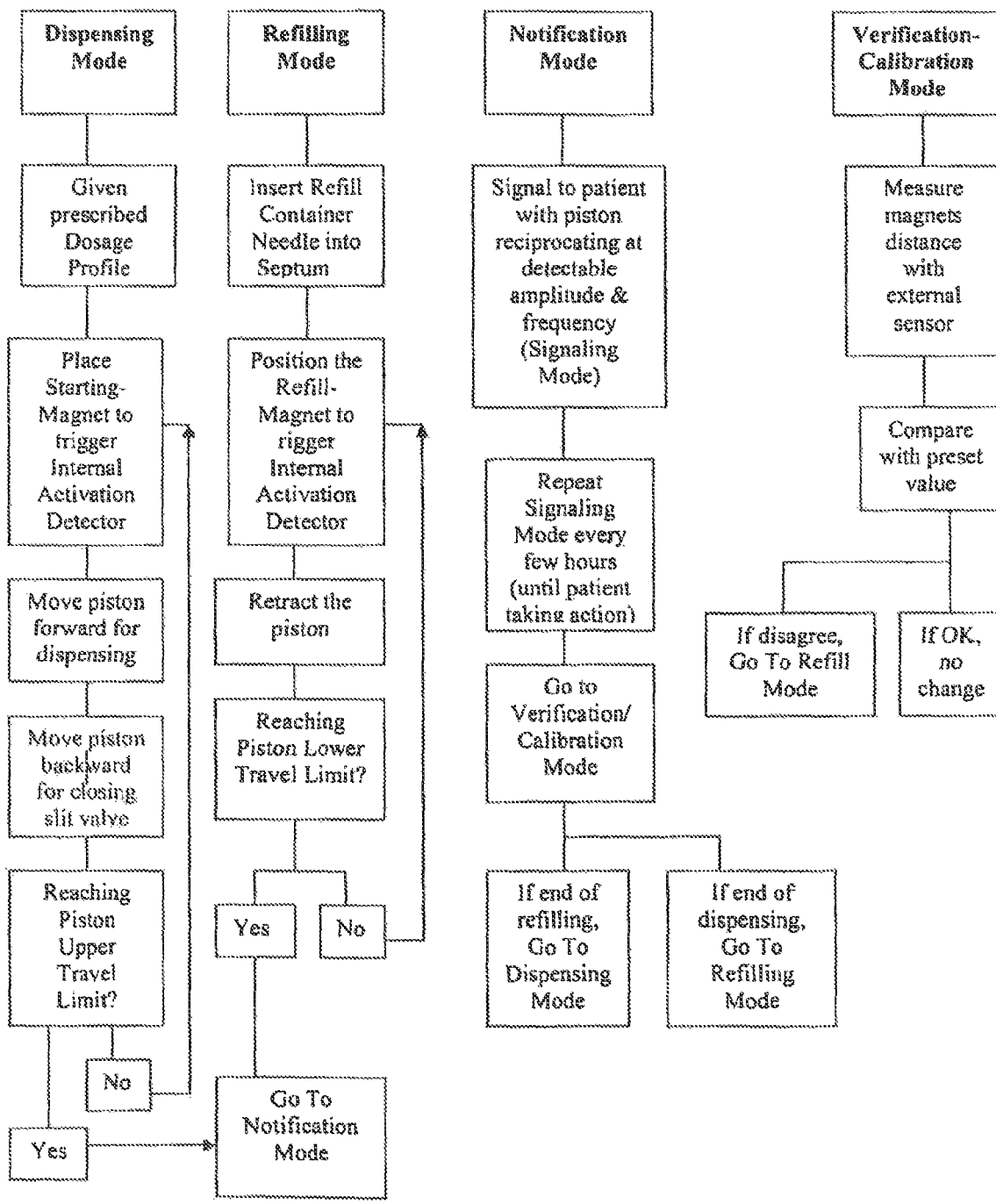
FIG. 5 is a control chart of operation modes of an implantable drug delivery pump device of the present invention.

As a summary, FIG. 5 shows the interactions of the operation modes of the software control program of the implantable drug delivery pump device of the present invention.

In summary, the implantable drug delivery pump device of the present invention provides a drug reservoir chamber having a piston and a filler chamber having a collapsible wall to facilitate the dispensing motion of the piston. With a slit valve attached to the catheter dispensing end, the software controlled retraction motion of the piston enables positive closing of the dispensing valve to prevent clogging and for refilling of the drug reservoir. The Notification Mode activates detectable oscillation of the piston to alert the user to take refilling actions. The verification and calibration feature uses external measurement of the distance between two magnets in the pump device to ensure reliable performance of the pump device of the present invention.

Although the invention has been described with reference to particular embodiments, the description is only an example of the invention's application and should not be taken as a limitation. Various other adaptations and combinations of features of the embodiments disclosed are within the scope of the invention as defined by the following claims.

Divided-Drug-Chamber Device Configuration

Figure 7B:
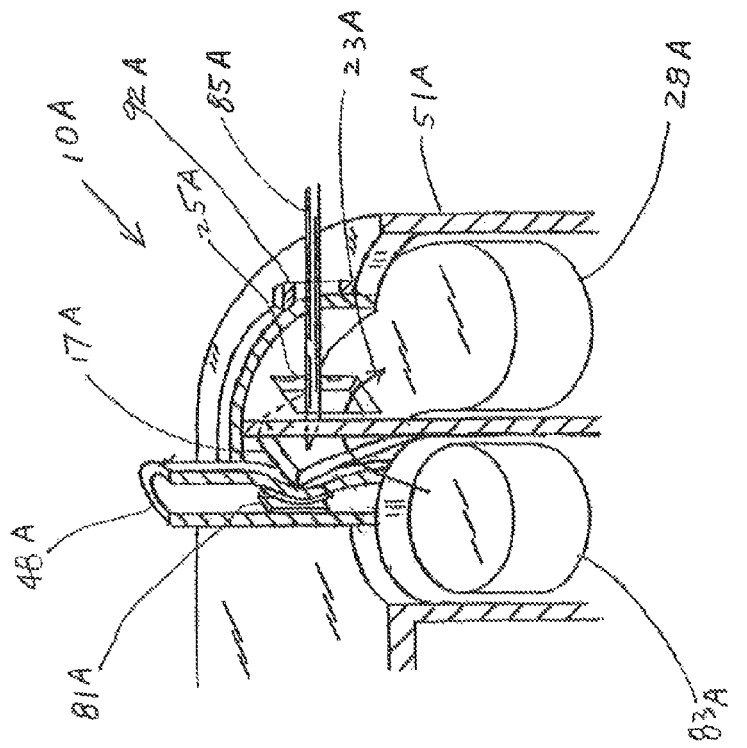
Figure 7A:
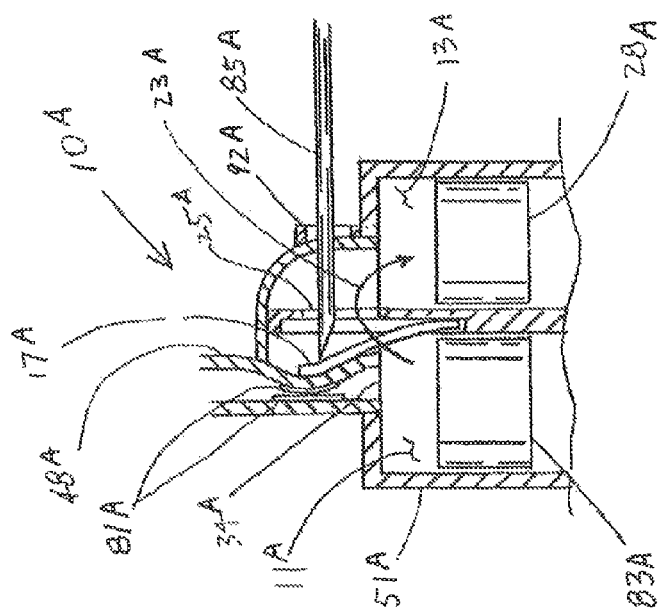
FIG. 7a is an enlarged cross-section view of a flap-type one-way valve of FIG. 6c with a refill container needle.

The infusion pump of this invention comprises a divided first chamber containing a first fluid and a second chamber, enclosed partially by collapsible walls, that contains a second fluid. FIGS. 6a, 6b and 6c show an infusion pump 10A of the present invention including housing walls 14A that encompass first chamber 18A containing first fluid 20A and second chamber 22A containing second fluid 24A. The first chamber 18A is a drug reservoir containing first fluid 20A and it is divided into a first compartment 11A and a second compartment 13A by a wall 15A mounted with a one-way valve 17A. FIG. 6b shows a top cross-section view of the division between the two compartments 11A and 13A by the wall 15A and the one-way valve 17A. FIG. 6c shows the extension of the dividing wall 15A and the one-way valve 17A into septum 44A of the implant device 10A. The one-way valve provides a flow path 23A as shown in FIG. 7a and FIG. 7b between the first and the second compartments 11A and 13A when the valve 17A is in the open position. The first compartment 11A has a piston 83A connected to a driving means and the second compartment 13A has a follower 28A, which is in flow communication with the movement of the piston 83A The wall of the second chamber 22A is collapsible as represented by a bellows wall 56A as shown in FIG. 6a. The second fluid 24A, which is inert to the drug fluid and body tissues, serves as a filler fluid in communication with the first fluid chamber to fill the space evacuated by the movements of the piston and the follower to prevent creation of a partial vacuum that could negatively impact the movement of the piston and the follower. Both piston 83A and follower 28A separate second fluid 24A from first fluid 20A. The piston is driven by a drive means for infusing the first fluid through outlet 34A and reducing the volume of the first fluid in the first compartment. In this divided drug chamber configuration, the drug dosage dispensed at each step of the piston forward movement is a small fraction of the amount for an un-divided configuration.

Furthermore, a catheter 48A is attached to outlet 34A of first chamber 18A in communication with the first fluid 20A. The wall 51A of the first chamber includes a filling septum 44A for inserting needle 85A of a refill container to inject a refill drug into the drug chamber. An outlet valve in a form of a slit-valve 52A is attached at the dispensing end of the catheter. A normally-closed slit-valve prevents backflow of fluids from the external environment into the device. The slit-valve is forced open by the forward movement of the piston exerting pumping pressure allowing the drug to be dosed from the reservoir to the treatment site. The implantable device is implanted into a patient's body, and the catheter can be led to a treatment location where the drug is dispensed. Depending on the geometry and the stiffness of the slit-valve elements, the slit-valve may be partially or fully open corresponding to the steps of the piston advancement. Following a step of dispensing drug, if further piston advancement is minute the slit-valve may be partially open without further dispensing the drug fluid out of the catheter. Being immersed with the dispensed drug still at the valve exit, the drug inside the valve opening is not mixed with the body fluid, which has been pushed away from the valve opening.

Reciprocating Piston Motion

The piston performs a reciprocating motion under the control of a motor driver that is mounted in an IC control board 32A as shown in FIG. 6A, and is preprogrammed. The first fluid is pushed by the forward movement of the piston. The perimeter surface of the piston is in sliding-sealing fit, represented by O-ring 61A, with the inner wall surface of the first compartment. The sliding-sealing fit or the wiping contact of the piston perimeter surface with the inner wall of the first compartment ensures no residual trace of drug fluid, i.e. the first fluid, comes in contact with the filler fluid on the opposite side of the piston. During the forward motion of the piston the one-way valve is forced to close and the slit-valve at the end of the catheter is forced to open to dispense the first fluid. During the backward motion of the piston a partial vacuum is created in the first compartment that causes the slit-valve to close and the one-way valve to open. As a result, the first fluid 20A from the second compartment 13A enters the first compartment IIA through the valve opening 25A (shown in FIG. 7a). Simultaneously, the follower 28A in the second compartment 13A moves forward, which induces the filler fluid 24 to fill the space left by the movement of the follower through the flow gaps 64A to fill the space left by the movement of the piston. The sliding-sealing fit or the wiping contact of the follower perimeter surface with the inner wall of the second compartment ensures no residual trace of drug fluid comes in contact with the filler fluid.

The filling motion of the filler fluid into the first and the second chambers reduces the volume in the second chamber, thereby, causing the bellows or the collapsible wall 56A to contract. With the slit-valve closed further retraction of the piston is hindered due to the partial vacuum created inside the first compartment. For a given drug dosage at each infusion event, the number of forward pulses and the immediate number of backward pulses can be predetermined for the device to provide the desired net amount of drug dispensed at the event through the slit-valve. In subsequent repeated reciprocating motion of the piston, the first fluid is incrementally dispensed and the follower is moving forward in each cycle. This process continues until the second compartment is empty. In the empty state, the space behind the follower is full of the filler fluid.

The dispensing process can start only when an activation detector is activated. The permanent magnet 92A mounted on septum 44A as shown in FIG. 6c is attached with an internal magnet proximity sensor (not shown) to function as an activation detector for triggering the controller and the motor driver in control board 32A. The use of a magnet proximity sensor using Hall Effect for tuning the operational gradient of the magnetic field normal to the face of the detector is known in the art. Commercially magneto-resistive sensors of the Honeywell Company may be used as an activation detector. These sensors have a high sensitivity with conventional magnets like AlNiCo and ceramic materials and their Wheatstone bridge elements convert the magnetic field direction into a voltage output. Optionally, a Reed Sensor of Cherry Corporation may be used as a magnetically activated switch. The internal magnet proximity sensor (not shown) is in electrical communication with the motor driver and the microprocessor in the IC board of the pump device. To save space in the septum area the Hall Effect circuit of the magnet proximity sensor is integrated in the IC board 32A. When a specified starter-magnet, for activating the pump device, is placed on top of the magnet ring 92A of the pump device 10A across the skin (not shown), the activation detector (not shown) detects the change of the magnetic field surrounding the magnet ring 92A and the circuit of the proximity sensor converts the change of magnetic field into a voltage output. The activation detector triggers the controller and the motor driver to start the dispensing function of the pump device.

Priming Steps

To avoid dead spaces, voids or air pockets in a drug delivery device of the present invention, the priming steps for complete filling of the device with drug fluid and filler fluid are as follows.

Referring to a preferred embodiment as shown in FIGS. 9a, 9b and FIGS. 10a, 10b, 10c, 10d and to start with a new and empty condition and before implanting the device, 1) squeeze and keep the slit valve at open condition, then move follower 128A to the lower travel limit, i.e. the bottom home position, 2) move piston 183A to the upper travel limit position, 3) insert an active plunger syringe pre-filled with the drug fluid to the tip of needle into septum 144A without opening one-way valve 117A (shown in FIG. 10c), 4) inject the drug fluid to fill up second compartment 113A completely with any possible air bubbles rising (not shown) against the gravity direction in the septum cavity, 5) with the slit valve remaining open, push the syringe needle further to open the one-way valve, 6) inject drug fluid to fill up the septum and the catheter and expel the air through the slit valve 52A, 7) release the slit valve to resume its self-closing position and retract the piston all the way to the lower travel limit to draw the drug fluid to fill the first compartment completely, 8) remove the syringe from the septum, 9) insert an active-plunger filler fluid syringe needle into the injection port of the filler fluid chamber at the gap under the follower, 10) insert vent needles (not shown) through the wall of the filler fluid chamber at extreme locations of the injection flow path of the filler fluid from the filler fluid injection port for venting air, 11) inject the filler fluid to fill up the filler fluid chamber completely and expel the air through the vent needles, 12) remove the filler fluid syringe and the vent needles. Alternatively, the evacuation of the air can be facilitated by a vacuum means attached to the vent needle during the injection of the filler fluid into the chamber. In addition, the wall areas for inserting the vent needle and the filler fluid syringe needle are of resilient material, which is penetrable and self-closing when the needles are removed. After the above priming steps the device is completely filled with the drug fluid in the first and second compartments of the drug chamber and with the filler fluid in the filler fluid chamber without any dead spaces, voids or air pockets in the device.

Refilling Process

Refilling of the first chamber can be accomplished by inserting a refill container 84A into the septum 44A of the pump device 10A as shown in FIGS. 8c and 8d. The septum has a raised ring (not shown) to facilitate the positioning of the needle through the skin. FIGS. 8a, 8b, 8c and 8d illustrate a sequence of refilling steps. FIG. 8a shows an implantable drug delivery pump device 10A of FIG. 6c at full state with both the piston 83A and the follower 28A at their home positions. The home position of the follower is the lower travel limit of the follower. A forward movement 60A of the piston 83A toward the slit-valve 52A causes the slit-valve to open under the pumping pressure as shown in FIG. 8b. After repeated forward and backward movements of the piston the first chamber becomes empty as shown in FIG. 8b where the follower 28A reaches the top 35A of the second compartment 13A. The top of the second compartment is the upper travel limit of the follower. To refill the device, a refill container 84A containing refill drug 37A is inserted into the septum 44A of the device 10A as shown in FIG. 8c. Referring to enlarged views of the flap-type one-way valve mechanism 17A as shown in FIGS. 7a and 7b, correct positioning of the refill container enables the needle 85A to push open the one-way valve 17A toward the catheter wall 48A. Further pushing of the needle 85A causes the catheter wall 48A to block the flow of the first fluid 20A into the catheter 48A. Forcing the catheter walls 48A to touch also enables the contact of two thin electrode elements 81A forming a contact switch, which is in electrical communication with the motor driver in the IC control board 32A, to activate the reciprocating or pumping motion of the piston. As a reverse of the dispensing function, retraction or backward movement of the piston draws the refill fluid 37A from the refill container 84A into the first compartment 11A and a subsequent forward movement pushes the refill fluid from the first compartment 11A into the second compartment 13A through the valve opening 25A. A series of reciprocating motion of the piston draws in the refill fluid from the refill container and delivers it into the second chamber until both the first and the second chambers are full of the refill fluid. Simultaneously during the refilling process the filler fluid 24 is returned to the bellows through the flow gap 64A, which is in communication with the filler fluid behind the piston and the follower and the filler fluid in the bellows. During these fluid movements the catheter entrance remains closed by the contact of the refill container needle against the catheter walls. The refill container is preferably a passive type not using an externally-actuated plunger, which is a safety feature for avoiding any accidental injection. As shown in FIG. 8c, refill container 84A uses internal disc 87A, which is in sliding fit with the inner wall of the container, for compacting drug fluid 37A. FIG. 8c shows refill container 84A being full of refill drug fluid 37A in the beginning of the refilling process. After completion of the refill process the refill container is depleted of the drug fluid and pulled from the septum as shown in FIG. 8d. At the completion of a refilling process and when the first chamber is full, the piston and the follower are at their home positions and the bellows is at its fully expanded shape.

Figure 7C:
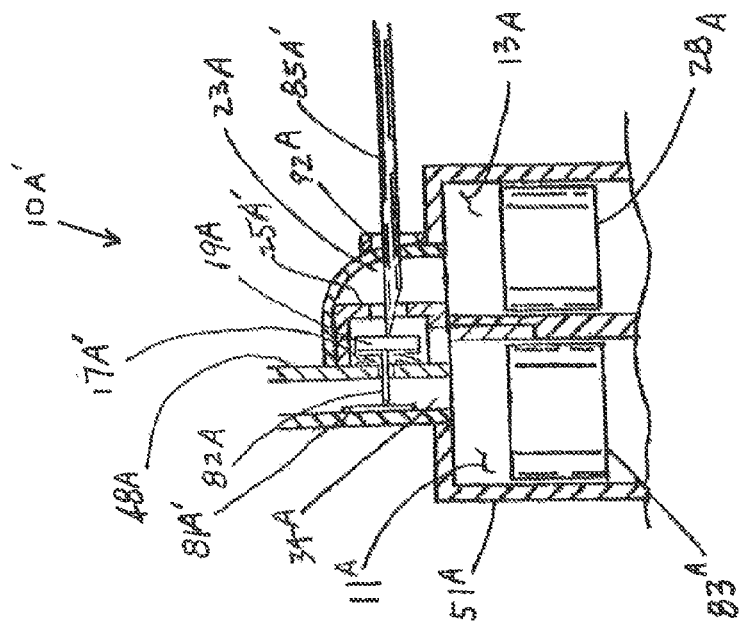
FIG. 7c is an enlarged cross-section view of a plunger-type one-way valve not touched by a refill container needle.
Figure 7D:
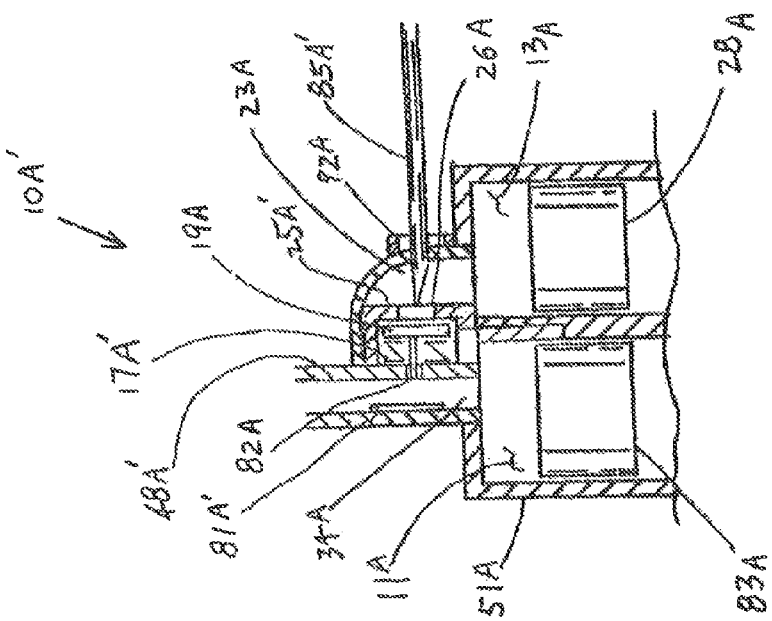
FIG. 7d shows the plunger-type one-way valve of FIG. 7c being pushed by the needle of the refill container against the electrode plate on the catheter wall blocking the flow channel.

Instead of using the flap-type valve 17A as shown in FIG. 7a, a plunger-type valve in a divided drug chamber of an implantable drug delivery device 1OA' as shown in FIGS. 7c, 7d can be used for closing the flow path in the catheter channel by the insertion of the needle of a refill container. Correct positioning of the refill container enables the needle 85A' to push open the plunger 19A toward the catheter wall 48A'. The plunger 19A is attached with an electrode-plate 82A and loaded with springs 17A'. Further pushing of the needle 85A' causes the electrode-plate 82A to block the flow of the first fluid 20A into the catheter 48A'. Forcing the movable electrode-plate 82A to touch stationary electrode 81A' also enables forming a contact switch, which is in electrical communication with the motor driver in the IC control board 32A, to activate the reciprocating or pumping motion of piston 83A. The slidable electrode plate 82A is a thin plate to minimize the displacement of the drug fluid in the catheter and the displaced volume may enter the septum area through the clearance between the electrode plate 82A and the catheter wall 48A'. This feature prevents the drug fluid being forced through the catheter valve 52A (shown in FIG. 6A) by the insertion of the needle. Upon release of the needle, the springs force the plunger against the partition wall 25A', which divides piston chamber 11A and reservoir chamber 13A in the septum area and has opening 26 for the insertion of the needle. With the use of the contact switch, a conventional active plunger-type syringe may be used for refilling as pushing of the plunger may assist pushing the drug into the drug chamber in addition to the vacuum force created by the withdrawing of the piston in the refilling process triggered by the contact switch.

Flexible-Layer Filler-Fluid

Instead of a bellows configuration positioned at the bottom end of a device such as the bellows 56A shown in FIG. 6a, the collapsible wall of the second chamber containing the second fluid may be a flexible and soft layer 156A attached to the housing walls 114A forming an external fluid chamber of the device 100A as shown in FIGS. 9a, 9b and 9c. FIG. 9b shows the flexible layer of the second chamber 122A attached externally to the housing walls 114A of the implantable device 100A of the present invention. Preferably the flexible layer is wrapped from the front side 116A, around the bottom side 118A, to the back side 119A of the housing walls 114A as illustrated in FIG. 9b. Side walls 132A and 134A and top wall 136A which is mounted with the septum 144A and the catheter 148A are not attached with a soft layer for ease of manufacturing and manual handling prior to implantation procedures. With respect to the flexible external fluid chamber, the first fluid chamber is referred as the internal fluid chamber. In comparison with the bellows configuration as shown in FIG. 6a the flexible-layer configuration has the advantage of shorter device length and more conformable contact with body tissues. FIGS. 9b and 9c also show the filler-fluid openings 170A and 172A. The first filler-fluid opening 170A on the first compartment wall 180A is for the entrance and exit of the second fluid 124A behind the piston 183A as the piston moves forward and backward, respectively. On the other hand, the second filler-fluid opening 172A on the second compartment wall 182A is for the entrance and exit of the second fluid behind the follower 128A as the follower moves forward and backward, respectively, following the piston movement.

Openings for the Passage of Filler Fluid

Specifically, FIGS. 10a, 10b, 10c, and 10d show the contraction and expansion of the external soft layer 156A containing the filler fluid 124A in a sequence of the refilling process of device 100A. FIG. 10a shows an implantable drug delivery device 100A of FIG. 9b at the full state with both the piston and the follower at their home positions. A forward movement as indicated by the arrow 160A of the piston 183A toward the slit-valve 52A causes the slit-valve to open under the pumping pressure. After repeated forward and backward movements of the piston the second compartment 113A is depleted of first fluid 120A and the space behind the follower 128A is filled with second fluid 124A as shown in FIG. 10b. For refilling, a needle 185A of refill container 184A containing refill drug 137A is inserted into the septum 144A of the device 100A as shown in FIG. 10c. Correct positioning of the refill container enables the needle to push the one-way valve 117A toward the catheter wall. Further pushing of the needle 185A causes the catheter walls 149A to block the flow of the first fluid into the catheter. The touching of the catheter walls also enables the contact of two thin electrode elements 181A, which are in electrical communication with the motor driver in IC control board 132A, to activate the reciprocating motion of the piston 183A. During retraction or backward movement 162A of the piston, as shown in FIG. 10c, the drug fluid inside the refill container is drawn into the first compartment while the refill drug inside the second compartment is held back by a partial vacuum as the device is enclosed by body tissues. The refill container is at atmospheric pressure because of the presence of a vent hole (not shown), The next forward movement of the piston pushes the first fluid into the second compartment, similar to flow path 23A indicated in FIG. 7a, through the edges of the one-way valve opening, which is similar to valve opening 25A indicated in FIG. 7b. A series of such reciprocating pumping motions can draw the filler fluid from the soft-layer second chamber through the first and second filler-fluid openings to fill the space behind the piston and the follower. At the completion of a refilling process as shown in FIG. 10d, the refill container 184A is empty, the piston and the follower are at their home positions and the soft-layer chamber is at its fully expanded shape.

Materials of Device Components

Referring to FIG. 6a, walls 54A of the first chamber and collapsible walls 56A of the second chamber are impermeable to external fluids present in a body tissue environment. In particular, wall 54A of first chamber 18A is made of a drug-compatible, implantable material of sufficient rigidity without deformation so as not to hinder the movement of the piston inside the reservoir chamber. For example, the wall material of the first chamber may be constructed from a metal, such as titanium, nickel titanium, stainless steel, anodized aluminum, or tantalum, or a plastic, such as polyethylene, nylon. However, collapsible wall 56A of second chamber 22A is made of flexible material such as silicone or polyurethane, which allows the wall to expand or collapse as fluid goes in and out of the second chamber. For self-sealing the septum is made of resilient material. Referring to FIGS. 7a and 7b septum 44A has a raised ring ridge for positioning the refill through the skin. The raised ring ridge may be in the form of ring magnet 92A of a polarity that attracts a ring magnet (not shown) of opposite polarity mounted on the needle 85A of the refill container 84A. The attraction between the two ring magnets having opposite polarities across the skin can facilitate positioning and stabilizing the refill container needle during the refilling process. The device is implanted preferably near the treatment site and the slit-valve is to be located at the treatment site. In a preferred embodiment the positive-closing slit-valve 52A is a molded dome-shaped cap of elastomeric materials having a cross-slit cut forming a plurality of flexible flappers. In a preferred embodiment a slit-valve used for the implantable drug delivery pump of this invention is of biocompatible silicone material. The slit-valve has a tubular wall base and four flappers. Each flapper is a curved triangular valve segment extending from the tubular wall base with the tip of each valve segment intercepting at the center, i.e. at the apex of the slit-valve opening when the slit-valve is at the closed position. Each valve segment can be bent like a cantilever beam under the pressure of a dispensing flow. The slit length, wall thickness and the elastic modulus of the valve material are designed to ensure self-closing of the slit-valve by the resiliency and the vacuum force in the absence of pumping pressure. With the use of a slit-valve, it is not necessary to use an outlet check valve to prevent backflow.

Battery

An implantable battery used in an implantable pump of the present invention needs to be encapsulated to avoid harmful leaks and diffusion. Generally an implantable pump requires milliampere level current pulses over a constant microampere level background drain. Examples of commercially available implantable batteries are lithium/thionyl chloride and lithium/carbon mono fluoride batteries made by GreatBatch, EaglePicher Medical Power and other manufactures. A Li/CFx battery, which is typically used for pacemakers, neuro-stimulation applications at milliampere application ranges, has a typical lifetime of five to six years. A small implantable battery by EaglePicher achieves a miniature cylindrical size of 0.260" long×0.090" diameter that can be packaged inside a pump device with a traditional implantation surgery or implanted at a separate nearby location via a minimally-invasive catheter procedure.

A preferred embodiment of a battery pack to be used for the present invention is a battery assembly comprising a first battery portion and a second battery portion and a battery-low circuit for switching to the first battery portion for battery-low notification. The first battery has a higher capacity than the second battery with the voltage across the first battery being greater than the voltage across the second battery. The battery assembly is connected to a pickup inductive coil in the implantable drug delivery device, which can be charged by magnetic flux produced by the inductive coil of an external battery charger across the skin. The battery pack includes a current limiting circuit having a current limiting resistor for self-regulating and preventing overcharge. The implantations of the battery-low circuit and the recharging of the battery by induction means are well known in the skill of the art.

Pump Size

With the advancement of miniaturization technologies, small electrical and mechanical components as well as a concentrated drug formulation can be packaged into a compact size for an implantable device of the present invention. For a commercially available piezoelectric motor, such as SQUIGGLE SQ-306 model by New Scale Inc., the motor size is 10 mm in length and 4 mm in diameter. Its motor driver in an IC control board including ASIC, resonant inductors, Boost circuit and FWD diode developed by Austria Microsystems can be packaged into 10 mm×10 mm×1.5 mm size. The motor can achieve a minimum linear shaft increment of 1 micrometer. With a piston head of 4 mm diameter this minimum increment of 1 micrometer movement results in the dispensing of 12.56 nano-liters fluid volume. With the capability of dispensing drug at the nano-liter scale, the drug chamber size of the drug delivery device can be minimized utilizing the full potential of concentrated or nanoparticle drug formulations as well as for supplying significantly longer period of use before refilling. Using other small components such as, a small implantable battery by EaglePicher which has a miniature cylindrical size of 0.260" long×0.090" diameter, enables packaging the key components of the drug delivery device into a compact system for implant applications.

Notification Mode

For a given drug chamber size and a given infusion profile for a patient, the refill interval is known, therefore, the time to refill can be planned. However, if refill does not occur in the appropriate time interval, a notification signal can be sent to the patient by the implantable drug delivery device of this invention. The notification feature utilizes the reciprocating motion of the piston. The motor driver can be programmed for a notification mode. In notification mode the motor driver retracts the piston for a predetermined distance then, with the self-closing slit valve remaining at the closed position, performs a small reciprocating motion of the piston with amplitude not exceeding the retracted distance such that no amount of drug fluid is dispensed out of the slit valve. The amplitude and the frequency of the reciprocating motion are preset so as to generate a vibration of the device that does not cause any harm but is detectable by the patient. Conditions for the notification mode include the end of dispensing cycle for refilling and battery low. For a predetermined battery low condition the built-in battery-low circuit in the control microprocessor triggers the notification mode. As a reminder for the patient to refill the device the reciprocating motion may be repeated to signal at a prescribed interval, which is to be determined (TBD) for a patient using the device. For instance the notification mode or the oscillation of the piston may be programmed to repeat at every 12 or 24 hours, depending on the patient's dependency on the drug and other factors such as to coincide with convenient day time schedules for taking action.

Verification

Additionally, there are a number of factors that may cause performance failures of an implanted device. These factors include malfunction of electronics, hesitation in piston movement, voids in the drug reservoir and possible clogging at the dispensing opening. Therefore, an independent verification of the performance of an implant device is essential to ensure reliable and predictable performance of the device. For verification of the pump performance of the present invention the position of the piston or a residual amount of dispensing material in the first chamber can be measured externally. As shown in FIG. 6c follower 28A is fitted with a second magnet 76A and the displacement of a magnet mounted on top of the follower can be determined by measuring the distance 78A between the second magnet 76A and the first ring magnet 92A, which is positioned at the center of the septum. The distance between two magnets can be measured by an external magnetic proximity sensor. A magnetic proximity sensor can be a commercially available Honeywell HMC1501 or HMC1512 magneto-resistive sensors. These sensors feature Wheatstone bridge elements to convert a magnetic field into a voltage output. The HMC sensors provide reliable performance in accuracy and resolution.

Software Control Elements

The control software in the microprocessor controller of the present invention is programmed to provide Dispensing Mode, Refilling Mode, Notification Mode and Verification-Calibration Mode. In the Dispensing Mode, the microprocessor commands to provide pulses of different durations to control the dispensing rates depending on a prescribed dosage profile, which are converted into a set of operational parameters for the operation of the motor driver. At each dispensing command, after the pre-determined forward pulses, a pre-determined number of backward pulses follows to ensure positive-closing of the slit valve. The required number of backward pulses for closing the slit valve is less than the number of forward pulsed for dispensing such that the desirable amount of drug dosage is dispensed. The schedules and timings of the controller action are based on inputs from an IC oscillator timer built in the IC board of the pump device. The IC circuit for an oscillator timer is well known in the art. With an external controller, the operational parameter set (OPS) in the implant pump of the present invention can be changed as needed. In addition a memory chip in the pump device records the history of forward and backward pulses. An algorithm is provided in the control program to monitor the current amount of drug remaining in the reservoir such that the timing for refilling the reservoir is determined. The maximum travel distance of the piston between the reservoir full and reservoir empty is converted into the maximum number of dispensing pulses, which is pre-programmed with a safety factor in the controller. When the maximum number of dispensing pulses is reached, no further forward movement of the piston is commanded.

In the Refilling Mode, upon trigging the refill switch by the insertion of the refill container needle, the controller microprocessor of the device of the present invention commands the motor driver to start the reciprocating motion of the piston. The duration of the refilling mode is preprogrammed for complete filling of the reservoir.

The Notification Mode can be programmed for repeated vibration of the pump device to alert the patient to take action to have the pump device refilled. The piston oscillation is initiated at the end of the Dispensing Mode, therefore, no additional drug is dispensed from the slit valve at the Notification Mode. The reciprocation of the piston is operated at detectable amplitude and frequency for a short duration such as a few seconds. The objective is to create vibrations which do not cause any harm or discomfort to the patient but are adequate to alert the patient to take action. At the Notification Mode, the command for the oscillation motion of the piston is repeated over a time interval.

In the Verification-Calibration Mode, the control program of the infusion pump of the present invention uses the input of a magnetic proximity sensor to measure the distance between the two magnets in the implant pump. The measured distance between the two magnets can be converted to the amount of drug fluid remaining in the drug chamber and compared to the expected value according to the prescribed dispensing drug profile. The control software program maintains the pre-scribed dispensing drug profile for a patient for operation of the motor driver. For a specified drug dispensing profile and knowing the time from the start of dispensing, the remaining amount of the drug fluid in the device can be determined, based on the geometry and size of the drug chamber, as an expected distance between the two magnets in the septum and in the piston. This expected distance is regarded as the expected profile value for comparing with the measured distance between the two magnets. If at any time a discrepancy exists, the pump device can be refilled to full state and to record new starting time for the device. Such verification and calibration steps may be taken several times to ensure the continuous use of the pump device according to the intended dispensing profile. The verification-calibration mode should be conducted prior to a routine refilling action.

Figure 11:
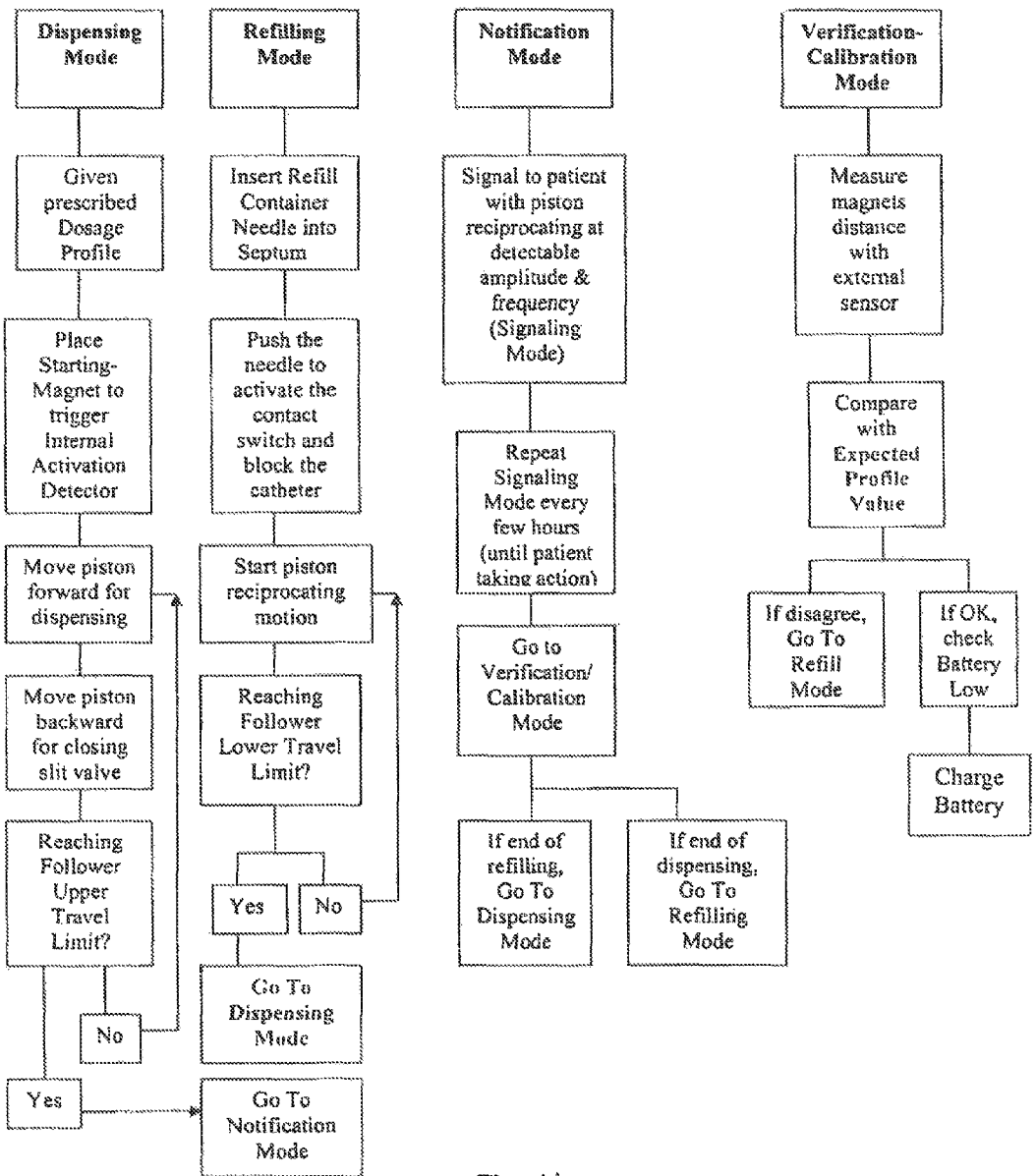
FIG. 11 is a control chart of operation modes of an implant infusion device of the present invention.

As a summary, FIG. 11 shows the interactions of the operation modes of the software control program of the implantable drug delivery pump of the present invention.

Although the invention has been described with reference to particular embodiments, the description is only an example of the invention's application and should not be taken as a limitation. Various other adaptations and combinations of features of the embodiments disclosed are within the scope of the invention. For example, a stepper motor may be used as a drive means instead of a piezoelectric motor as described in the present invention. Also, an external power source and external controller may be used to reduce the size of an implantable pump device of the present invention. In such case the pump device needs to include an antenna and a RF receiver. Alternatively, a smaller size may be achieved by separating IC board and battery from the pump mechanism and implanted at different location away from the basic pump mechanism.

Two-Drug-Chambers Device Configuration

An implantable dual drug delivery system of this invention features two drug chambers with different refill container-port identifications for matching with correct refill containers of the two drugs. In the following descriptions, first drug fluid and drug A fluid are used interchangeably. Second drug fluid and drug B fluid are used interchangeably. First chamber, drug A chamber and drug A reservoir are used interchangeably. External chamber, filler fluid chamber are used interchangeably.

Specifically an implantable dual drug infusion pump of the present invention has first drug chamber containing first drug fluid, second drug chamber containing second drug fluid and an external filler fluid chamber containing filler fluid. Each drug chamber is divided by a wall having a one-way valve into a first compartment and a second compartment. Each first compartment has a piston connected to a drive means and each second compartment has a follower, which is in flow communication with the movement of the piston.

The filler fluid chamber is attached externally to the drug chambers and it contains a filler fluid enclosed by collapsible soft layers. The soft layers are wrapped around housing walls of the drug chambers. The filler fluid is in flow communication with both the first compartment and the second compartment of each drug chamber for filling the space left by the movements of the pistons and the followers. Additionally, the pistons and the followers separate the filler fluid from the first drug fluid and the second drug fluid. The walls of the first and the second chambers as well as that of the external chamber are impermeable to outside fluids present in an operating environment.

Figure 12:
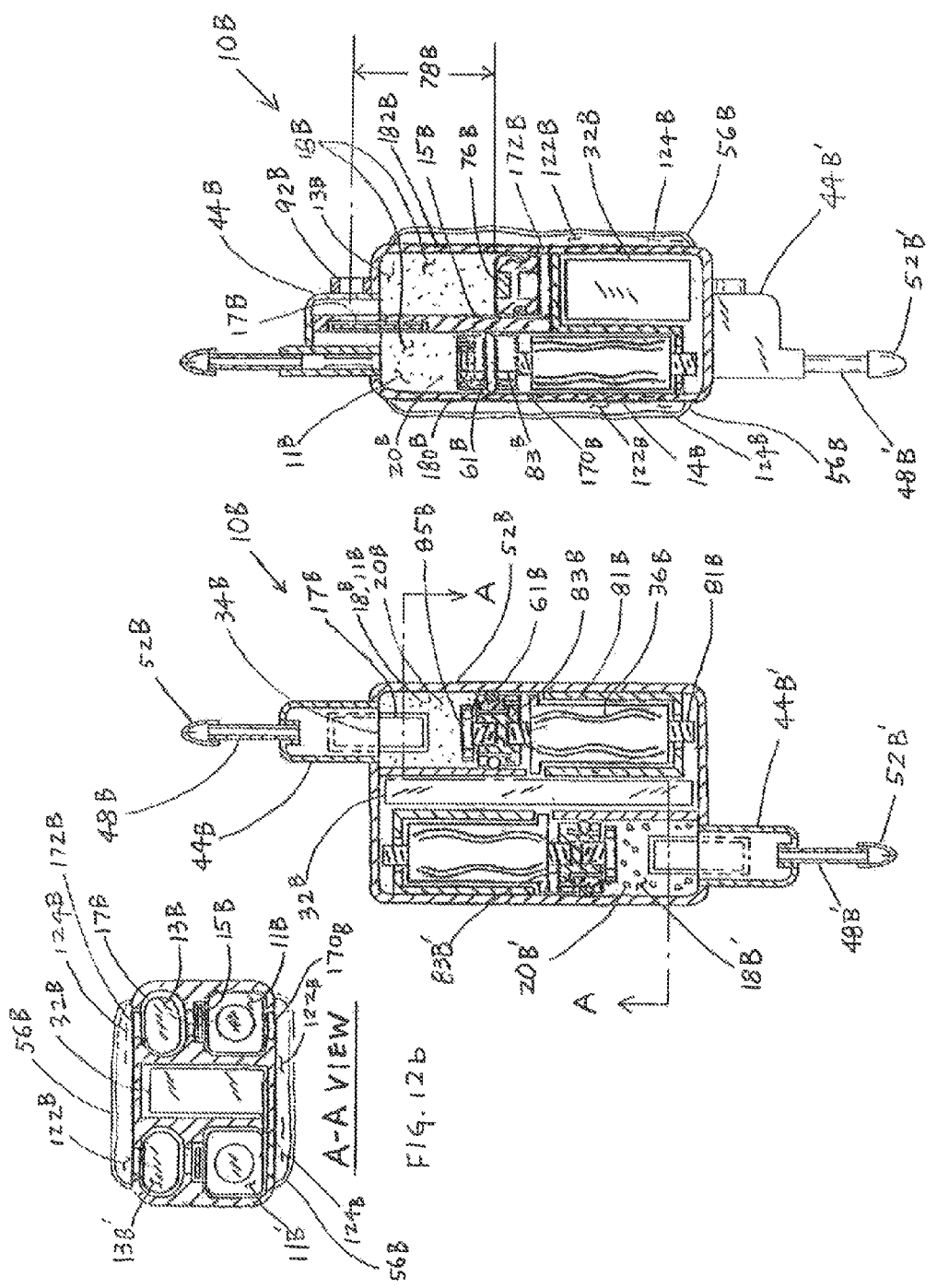

Referring to FIGS. 12a, 12b and 12c, the dual drug delivery device of this invention comprises two independent drug chambers, drug chamber A and drug chamber B, and one filler fluid chamber.

FIG. 12a shows drug A chamber 18B containing drug A 20 having catheter 44B with slit valve 52B and drug B chamber 18B' containing drug B 20B' having catheter 44B' with slit valve 52B'. These drug chambers and catheters are oriented in opposite directions. Drug A chamber and drug B chamber are of the same configuration and separated by a common IC control board 32B and their housing walls 14B are attached with an external chamber 122B containing filler fluid 124B. The drive mechanism for drug A piston 83B and drug B piston 83B' are the same. For simplicity, only the drug chamber configuration and the drive mechanism for drug A are described in FIG. 12c, which is a side cross-section view of the device of FIG. 12a. In FIG. 12a the drug A chamber 18B is divided into first compartment 11B and second compartment 13B by a wall 15B mounted with a one-way valve 17B.

Figure 13:
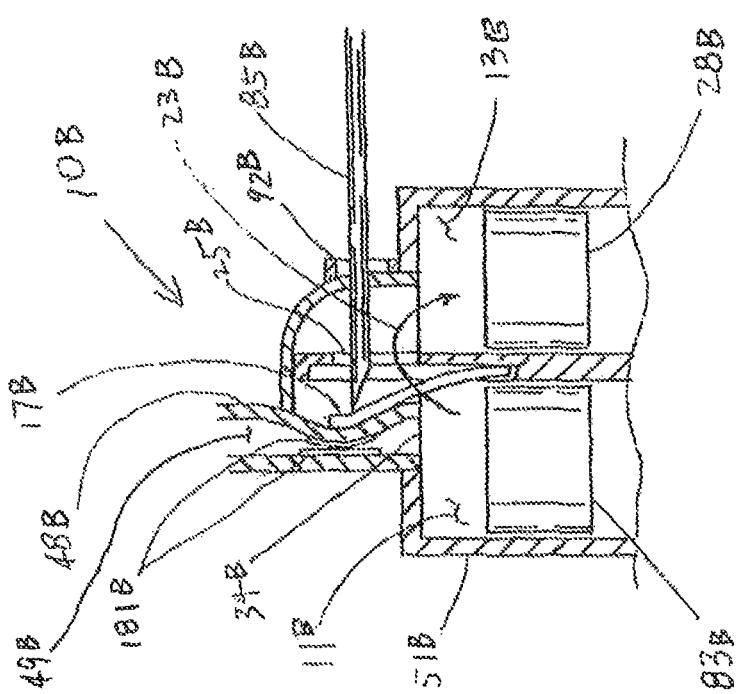
FIG. 13 is an enlarged cross-section view of the one-way valve of FIG. 12c with a refill container needle inserted.

FIG. 12b further shows a top cross-section view of the division between the two compartments 11B and 13B by the wall 15B and the one-way valve 17B for the drug A chamber, and the division between two compartments 11B' and 13B' for the drug B chamber. Also shown in FIG. 12c is an extension of the dividing wall 15B and the one-way valve 17B into septum 44B of the implant device 10B. In the enlarged view in FIG. 13, the flap-type one-way valve 17B provides a flow path 23B between the first and the second compartments 11B and 13B when the valve 17B is in the open position. The contact switch of electrodes 181B can be activated by the insertion of the needle 85B, which also causes the blocking of the catheter channel 49B. Alternatively, a plunger-type valve similar to that shown in FIGS. 7c, 7d for a divided drug chamber can be used for closing the flow path in the catheter channel by the insertion of the needle of a refill container. The first compartment 11B has a piston 83B connected to a drive means and the second compartment 13B has a follower 28B, which is in flow communication with the movement of the piston 83B.

Referring to FIG. 12c the external chamber 122B is segmented and attached externally to housing wall 14B. The external chamber 122B has an external soft layer which is collapsible. The filler fluid 124B, which is inert to the drug fluids and body tissues, is in flow communication with the drug chambers for filling the space evacuated by the movements of the piston and the follower to prevent creation of a partial vacuum that, if it were to exist, could negatively impact the movement of the pistons and the followers. Both piston 83B and follower 28B (shown in FIG. 13) separate filler fluid 124B from drug fluid 20B. The piston is driven by a drive means for infusing the drug fluid A through outlet 34B and reducing the volume of the drug fluid A in the first compartment. The above descriptions for the chamber configuration and the movements of the piston and the follower for drug A are applicable to that for drug B.

Moreover, referring to the drug A configuration, a catheter 48B is attached to outlet 341 of drug A chamber 18B in flow communication with the drug fluid 20B. The wall 51B of the drug A chamber includes a filling septum 44B for inserting needle of a refill container to deliver refill drug into the drug chamber. An outlet valve in a form of slit-valve 52B is attached at the dispensing end of the catheter. A normally-closed slit-valve prevents the backflow of fluids from the outside environment into the device. The slit-valve is forced to open by the forward movement of the piston exerting pumping pressure to force the drug exiting from the reservoir to the treatment site. Depending on the geometry and the stiffness of the slit-valve elements, the slit-valve may be partially or fully open corresponding to the forward steps of the piston advancement. If the piston advancement is at a minimal number of steps the slit-valve may be partially open without dispensing the drug fluid out of the catheter, Reciprocating Piston Motion The piston performs a reciprocating motion under the control of a programmable motor driver which is mounted in IC control board 32B as shown in FIG. 12a. Each drug fluid is pushed by the forward movement of its respective piston. The perimeter surface of each piston is in slidable sealing fit, represented by O-ring 61B, with the inner wall surface of the first compartment 11B. The sliding-sealing fit or the wiping contact of the piston perimeter surface with the inner wall of the first chamber ensures no residual trace of drug fluid left behind the piston that will come in contact with the filler fluid and similarly no residual trace of the filler fluid left on the opposite side of the piston that will contact with the drug fluid. During the forward motion of the piston the one-way valve is forced to close and the slit-valve at the end of the catheter is forced to open to dispense the drug fluid. During the backward motion of the piston a partial vacuum is created in the first compartment that causes the slit-valve to close and the one-way valve to open. As a result, referring to FIG. 12c, drug fluid 20B from the second compartment 13B enters the first compartment 11B through the valve opening 25B. Simultaneously, the follower 28B in the second compartment 13B moves forward.

The flow of the filler fluid 124B between the external chamber 122B and the drug A chamber 18B is through first and second filler-fluid openings 170B and 172B in housing walls as shown in FIG. 12b and FIG. 12c. The first filler-fluid opening 170B on the first compartment wall 180B is for the entrance and exit of the filler fluid 124B behind the piston 83B as the piston moves forward and backward, respectively. On the other hand, the second filler-fluid opening 172B on the second compartment wall 182B is for the entrance and exit of the filler fluid behind the follower 28B as the follower moves forward and backward, respectively, following the piston movement. The sliding-sealing fit or the wiping contact of the follower perimeter surface with the inner wall of a drug chamber ensures no residual trace of drug fluid left behind the follower that will come in contact with the filler fluid, and similarly no residual trace of the filler fluid left on the opposite side of the follower that will contact the drug fluid.

The filling of the filler fluid into drug A and drug B chambers reduces the volume in the external filler fluid chamber, thereby causing the collapsible soft layer 56B to contract. For a given drug dosage at each infusion event, the number of forward pulses and the immediate number of backward pulses can be predetermined for the device to provide the desired net amount of drug dispensed at the event through the slit-valve. In subsequent repeated reciprocating motion of the piston, the drug fluid is incrementally dispensed and the follower is moving forward in each cycle. This process continues until the second compartment is empty. In the empty state, the space behind the follower is full of the filler fluid.

The dispensing process can start only when an activation detector is activated. The permanent magnet 92B mounted on septum 44B as shown in FIG. 12c is attached with an internal magnet proximity sensor (not shown) to function as an activation detector for triggering the controller and the motor driver in control board 32B. The use of a magnet proximity sensor using Hall Effect for tuning the operational gradient of the magnetic field normal to the face of the detector is known in the art. Commercially magneto-resistive sensors of the Honeywell Company may be used as an activation detector. These sensors have a high sensitivity with conventional magnets like AlNiCo and ceramic materials and their Wheatstone bridge elements convert the magnetic field direction into a voltage output. Optionally, a Reed Sensor of Cherry Corporation may be used as a magnetically activated switch. The internal magnet proximity sensor (not shown) is in electrical communication with the motor driver and the microprocessor in the IC board of the pump device. To save space in the septum area the Hall Effect circuit of the magnet proximity sensor is integrated in the IC board 32B. When a specified starter-magnet, for activating the pump device, is placed on top of the magnet ring 92B of the pump device 10B across the skin (not shown), the activation detector (not shown) detects the change of the magnetic field surrounding the magnet ring 92B and the circuit of the proximity sensor converts the change of magnetic field into a voltage output. The activation detector triggers the controller and the motor driver to start the dispensing function of the pump device.

Priming Steps

To avoid dead spaces, voids or air pockets in a dual-drug drug delivery device of the present invention, the priming steps for complete filling of the device with drug A, drug B and filler fluid are as follows. Referring to a preferred embodiment as shown in FIGS. 16a, 16b and FIGS. 15a, 15b for priming the drug A chamber with reference to components for drug A and starting with a new and empty condition before implantation, 1) squeeze and keep the slit valve in the open position while moving follower 28B to the lower travel limit, i.e. the bottom home position, 2) move piston 83B to the upper travel limit position, 3) insert an active-plunger syringe, pre-filled with the drug fluid to the tip of the needle, into septum 44B without opening one-way valve, 4) inject the drug fluid to fill the second compartment completely with any possible air bubbles rising (not shown) against gravity in the septum cavity, 5) with the slit valve remaining open, push the syringe needle further to open the one-way valve, 5) inject drug fluid to fill the septum and the catheter and expel the air through the slit valve, 6) release the slit valve to resume its self-closing position and retract the piston to the lower travel limit to draw additional drug fluid from the syringe to fill the first compartment completely, 8.) remove the syringe from the septum. To prime the drug B chamber with reference to components for drug B, repeat above steps (1) to (8).

To prime the filler fluid chamber, with both the drug A and drug B chambers totally filled, 1) insert an active-plunger filler fluid syringe needle into the injection port of the filler fluid chamber at the gap below the follower, 2) insert vent needles through the wall of the filler fluid chamber at the extreme opposite location of the injection flow path of the filler fluid from the filler fluid injection port to vent air, 3) inject the filler fluid to fill the filler fluid chamber completely and expel the air through the vent needles until fluid exits the vent, 4) remove the filler fluid syringe and the vent needles. Alternatively, the evacuation of the air can be facilitated by a vacuum means attached to the vent needle during the injection of the filler fluid into the chamber. In addition, the wall areas for inserting the vent needle and the filler fluid syringe needle are of resilient material, which is penetrable and self-closing when the needles are removed. After the above priming steps the device is completely filled with the drug A in the drug A chamber, drug B in the drug B chamber and the filler fluid in the filler fluid chamber without any dead spaces, voids or air pockets in the device.

Refilling Process

FIGS. 14a, 14b, 14c, 14d show a sequence of the refilling process of device 10B including the contraction and expansion of the external soft layer 56B containing the filler fluid 124B. FIG. 14a shows an implantable dual drug delivery device 10B as described in FIG. 12c at the full state with both the piston and the follower at their home positions. The home position of the follower is the lower travel limit of the follower. A forward movement as indicated by the arrow 160B of the piston 83B toward the slit-valve 52B causes the slit-valve to open under the pumping pressure. After repeated forward and backward movements of the piston the second compartment 13B is depleted with drug A fluid 20B but filled with filler fluid 124B behind the follower 28B as shown in FIG. 14b. The top end of the second compartment is the upper travel limit of the follower. For refilling, a needle 185B of refill container 184B with refill drug A 137B is inserted into the septum 44B of device 10B as shown in FIG. 14c. Correct positioning of the refill container enables the needle to push open the one-way valve 17B toward the catheter wall. Further pushing of the needle 185B forces the catheter walls 149B to close and block the flow of the drug A fluid into the catheter. Contacting of the catheter walls also enables the contact of two thin electrode elements 181B, which are in electrical communication with the motor driver in IC control board 32B, to activate the reciprocating motion of the piston 83B. During retraction or backward movement 162B of the piston as shown in FIG. 14c only the refill drug A inside the refill container, which is compacted by slidable disc 185B at atmospheric pressure due to the presence of vent opening 186B, is drawn into the first compartment while the refill drug A inside the second compartment is held back by a partial vacuum as the device is enclosed by body tissues. The next subsequent forward movement of the piston pushes the first fluid into the second compartment, similar to flow path 23B in FIG. 13a, through the edges of the one-way valve opening. A series of such reciprocating pumping motions can draw in the filler fluid 124B from the soft-layer external chamber 122B through the first and second filler-fluid openings to fill the space behind the piston and the follower. At the completion of a refilling process as shown in FIG. 14d indicating an empty refill container 184B the piston and the follower are at their home positions and that the soft-layer chamber is at its fully expanded shape. Note that the refill container is of a "passive type" having no plunger thereby avoiding any accidental injection. Infusion from the refill container is possible only by the pumping action of the piston.

Failsafe Refill Container Feature

The refilling of the dual drug delivery device of the present invention preferably uses self-locking refill containers to prevent the injection of drug into the wrong drug chamber. To ensure the correct matching of a drug refill container with the septum of the same drug, magnets of opposite polarities are used to create an attraction force between the matched refill container and the septum. With a mismatched refill container and septum, a repelling force is created that locks the refill container. For clarity, a magnet of a septum of drug A chamber is used for illustration in FIG. 15a and FIG. 15b. The magnet is preferably a ring magnet which is hollow at the center for inserting the needle of the refill container through the septum. FIG. 15a shows attraction force 230B between the matched refill container A 284B and magnet 92B of the septum of the drug chamber for drug A. As a result, magnet 260B of the refill container is attracted to the magnet 92B of drug A chamber 18B, therefore, opening the flow path, as shown in FIG. 16a, from the reservoir 237B to drug chamber 18B.

The self-locking refill container 284B comprises a needle 285B, a tubular housing containing drug fluid 237B. The tubular housing includes a valve chamber 262B having an open end 261 B in communication with needle 285B and a reservoir chamber 264B which is attached with a slidable disc 289B forming an enclosed bottom. An orifice plate 240B is positioned between and separating valve chamber 262B and reservoir chamber 264B. Orifice plate 240B has orifice 255B at the center for passage of the drug fluid from the reservoir chamber to the valve chamber. The drug fluid is compacted by the slidable disc, which is at atmospheric pressure due to the presence of vent opening 291B. In a preferred embodiment the movable magnet 260B is an annular ring configuration. The annular magnet ring 260B has a top surface having a solid block area 252B in the center and a plurality of slot openings 250B surrounding the center block area 252B. The annular magnet ring 260B has a polarity that is opposite to the ring magnet 92B of the septum of the same drug such that the annular ring 260B is attracted away from the orifice plate 240B when the needle of the refill container is inserted into the septum of the correct drug chamber. When the top surface of the annular magnet ring is away from the orifice plate, a flow path is created for the drug fluid to be drawn into the drug chamber.

FIG. 15b shows a repelling force 232B between a mismatched refill container 284B' of drug B and ring magnet 92B of the septum of drug A chamber. The refill container 284B' of drug B has the same configuration as that of the refill container 284B of drug A except that the polarity of its annular magnet with refill drug A 137B is inserted into the septum 44 B of device 10B as shown in FIG. 14c. When needle 285B' of the refill container is inserted into the septum of drug A, its annular ring is repelled toward the orifice plate 240B' such that the solid block area 252B' completely blocks the opening of the orifice plate 240B'. As a result, the refill container of drug B is locked as the flow of the drug is blocked from flowing into the drug chamber A. All the ring magnet valves used in the refill container are to be coated with an inert, biomedical and drug compatible material to prevent reaction with the drugs delivered by the device.

Matched Filling Condition

A matched refilling condition is shown in FIG. 16a and FIG. 16b. FIG. 16a shows an implantable dual drug delivery device 10B of the present invention in which the polarity of the ring magnet 260B of the refill container 284B of drug A 237B is opposite to that of the septum ring magnet 928 of drug A chamber 18B. Due to the attraction force 230B between the two ring magnets 92B and 260B, the refill container 284B is unlocked internally when inserted into the septum. The contact of two electroplates 181B pushed by the refill container needle activates the motor driver in the IC control board 32B to start reciprocating motion of the piston 28B. The internal mechanism of refilling is as described previously on FIG. 14c and FIG. 14d. The refilling stops when the refill container A 284 B becomes empty 238B as shown in FIG. 16b or when the reciprocating motion of the piston reaches a predetermined time interval according to the software control program. FIG. 16b also shows that the soft layer 56B of the filler fluid 124B has been expanded fully and the refill container being removed from the septum.

In a mis-matched condition, FIG. 17a shows a dual drug delivery device 10B of the present invention being inserted with a refill container 284B of drug A into the septum 44b' of drug B chamber 18B', as indicated in FIG. 12a. In this case the polarity of the annular ring magnet of the refill container is the same as that of the septum. Therefore, the annular ring magnet ring 260B is repelled blocking the opening 255B in the base plate. As a result, the refill container 284B is internally locked so that the flow from the refill container is prevented. With correct matching, refill container 284B' of drug B 237B' should be used and the polarity of its annular ring magnet is opposite to ring magnet 92B' of septum 44B' of drug B as shown in FIG. 17b. FIG. 17c shows the completion of the refilling of drug B as the refill container 284B' is being removed from the septum 44B'.

Two Drug Chambers of Same Orientation

In the forgoing descriptions, two drug chambers and their catheters are aligned in opposite directions. Also, alternatively, each drug chamber may not be divided into two compartments by a wall having a one-way valve. FIG. 18a and FIG. 18b show an implantable dual drug delivery pump device 700B of the present invention having two drug chambers 718B and 718b and their catheters 748B and 748B' aligned in the same direction. Drug A chamber 718B and drug B3 chamber 718B' contain drug A 720B and drug B 720B', respectively, and each drug chamber is undivided. FIG. 18b is a top view from a cross-section showing spatial arrangement of the drug chambers 718B and 718B'. The pistons 783B and 783B' in the chambers are driven by motors 736B and 736B', which are driven by a common motor driver in the IC control board 732B. The operation of each drug chamber of the dual drug delivery device as shown in FIG. 18a is similar to that of dual-drugs delivery device having an opposite orientation as shown in FIG. 12a. However, the dispensing and the refilling actions for an undivided drug chamber 718B without using an internal one-way valve are simpler than that for a divided drug chamber 18B of FIG. 2a. For an undivided drug chamber configuration no reciprocating motion is required for piston movement to effect dispensing and refilling actions. Pistons 736B and 736B' are driven independently forward for predetermined number of steps to dispense the desirable drug dosage until the drug reservoir is empty. For refilling, after a refill container of the same drug is inserted, activating the contact switch for the piston of the same drug chamber, then the piston is automatically retracted to draw the refill drug fluid into the drug chamber until the drug chamber is full. Simultaneously the filler fluid 724B fills the space behind the piston during the dispensing mode and leaves the space during the refilling mode. Following the movement of the filler fluid the soft layer 756B of the filler fluid chamber contracts and expands in the dispensing mode and the refilling mode, respectively. In comparison with the divided drug chamber configuration, the minimum amount of drug fluid dispensed per piston advancement is higher than that of the undivided configuration. The selection of divided or undivided drug chamber depends on drug concentrations, frequency of infusion and the size limitation of the dual-drug pump device.

Ultrasonic Motor

A drive means of an implantable infusion delivery device of the present invention can be a threaded rod 81B driven by motor 36B as illustrated in FIG. 12a. The rotation of threaded rod 81B causes forward and backward movements of piston 83B corresponding to the rotational direction of the motor. Preferably motor 36B is a piezoelectric motor, which is illustrated in FIG. 12a comprising threaded rod 81B and piezoelectric plates (not shown) with one end forming a threaded-nut configuration (not shown). The vibration of the piezoelectric plates can cause the threaded rod to rotate. Threaded rod 81B is in free-to-rotate engagement with the piston 28B. Generally the piston may have non-circular cross-section undergoing linear movement without rotation. The conversion of rotational motion of thread rod 81B to linear motion of the piston is achieved by using a rotational sleeve and a retainer.

Materials of Device Components

Referring to FIG. 12a, walls 52B of the first chamber and collapsible soft layer 56B of and the filler fluid chamber are impermeable to external fluids present in a living tissue environment. In particular, walls 52B of drug chambers are made of a drug-compatible, implantable material of sufficient rigidity without deformation so as not to hinder the movement of piston inside the reservoir chamber. For example, the wall material of the drug chambers may be constructed from a metal, such as titanium, nickel titanium, stainless steel, anodized aluminum, or tantalum, or a plastic, such as polyethylene, nylon, or polyurethane. However, soft layer wall 56B of filler fluid chamber 122B is made of flexible material such as silicone, or polyurethane, which allows the wall to expand or collapse as fluid is added or withdrawn from the first chamber into the filler fluid chamber. For self-sealing the septum is made of resilient material. Preferably PDMS is selected for its flexibility and ability to reseal itself after repeated punctures via a refill container needle.

In implantation, a drug delivery device is implanted near the treatment site and the slit-valve is to be located at the treatment site. In a preferred embodiment positive-closing slit-valve 52B is a molded dome-shaped cap of elastomeric materials having a cross-slit cut forming a plurality of flexible flappers. In a preferred embodiment a slit-valve used for the implantable infusion pump of this invention is of biocompatible silicone material. The slit-valve has a tubular wall base and four flappers. Each flapper is a curved triangular valve segment extending from the tubular wall base with tip of each valve segment intercepting at the center, i.e. at the apex of the slit-valve opening when the slit-valve is at the closed position. Each valve segment can be bent like a cantilever beam under the pressure of a dispensing flow. The slit length, wall thickness and the elastic modulus of the valve material are designed to ensure self-closing of the slit-valve by the resiliency and the vacuum force at the absence of pumping pressure. With the use of a slit-valve, it is not necessary to use an outlet check valve for preventing backflow.

Software Control Elements

The control software in the microprocessor controller of the present invention is programmed to provide Dispensing Mode, Refilling Mode, Anti-Clogging Mode, Notification Mode and Verification-Calibration Mode. In the Dispensing Mode, the microprocessor commands for dispensing drug A and drug B are independent. For each drug the microprocessor sends commands to provide pulses of different durations for controlling the dispensing rates depending on a prescribed dosage profile and schedule for the drug, which are converted into a set of operational parameters for the operation of the motor driver for the drug. At each dispensing command, after the pre-determined forward pulses, a pre-determined number of backward pulses follow to ensure positive-closing of the slit-valve. The required number of backward pulses for closing the slit-valve is less than the number of forward pulses for dispensing such that the desirable amount of drug dosage is dispensed. The schedules and timings of the controller action are based on inputs from an IC oscillator timer built in the IC board of the pump device. The IC circuit for an oscillator timer is well known in the art. With an external controller, the operational parameter set (OPS) in the implant device of the present invention can be changed when the need of the patient changes. In addition a memory chip in the device records history of forward and backward pulses for each drug. An algorithm is provided in the control program to monitor the current amount of drug remaining in each drug chamber such that the timing for refilling each of the two drug chambers is determined. The maximum travel distance of the piston in a drug chamber in between the chamber full and chamber empty is converted into the maximum number of dispensing pulses, which is pre-programmed with a safety factor in the controller. When the maximum number of dispensing pulses is reached, no further forward movement of the piston is commanded.

In the Refilling Mode, upon triggering the refill switch by the insertion of a refill container needle in the septum of a drug chamber, the controller microprocessor of the device of the present invention commands the motor driver to start the reciprocating motion of the piston in the drug chamber. The duration of the refilling mode is pre-programmed for complete filling of the drug chamber.

The Notification Mode can be programmed for repeated vibration of the pump device to alert the patient to take action to have the pump device refilled. The piston oscillation is initiated at the end of the Dispensing Mode, therefore, no additional drug is dispensed from the slit valve at the Notification Mode. The reciprocation of the piston is operated at detectable amplitude and frequency for a short duration such as a few seconds. The objective is to create vibrations which do not cause any harm or discomfort to the patient but are adequate to alert the patient to take action. At the Notification Mode, the command for the oscillation motion of the piston is repeated over a time interval.

In the Verification-Calibration Mode, the control program of the dual infusion pump of the present invention uses the input of a magnetic proximity sensor which measures the distance between the two magnets in each drug chamber. The measured distance between the two magnets can be converted to the amount of drug fluid remaining in the drug chamber and compared to the expected value according to the prescribed dispensing drug profile. The control software program maintains the prescribed dispensing drug profile for a patient for the operation of the motor driver. For a specified drug dispensing profile and knowing the time from the start of dispensing, the remaining amount of the drug fluid in the device can be determined, based on the geometry and size of the drug chamber, as an expected distance between the two magnets in the septum and in the piston. This expected distance is regarded as the expected profile value for comparison with the measured distance between the two magnets. If at any time a discrepancy exists, each drug chamber of the dual pump device can be refilled to full state and a new starting time recorded for the device. Such verification and calibration steps may be taken several times to ensure the continuous use of the dual pump device follows the intended dispensing profile. The verification-calibration mode should be conducted prior to a routine refilling action.

Figure 19:
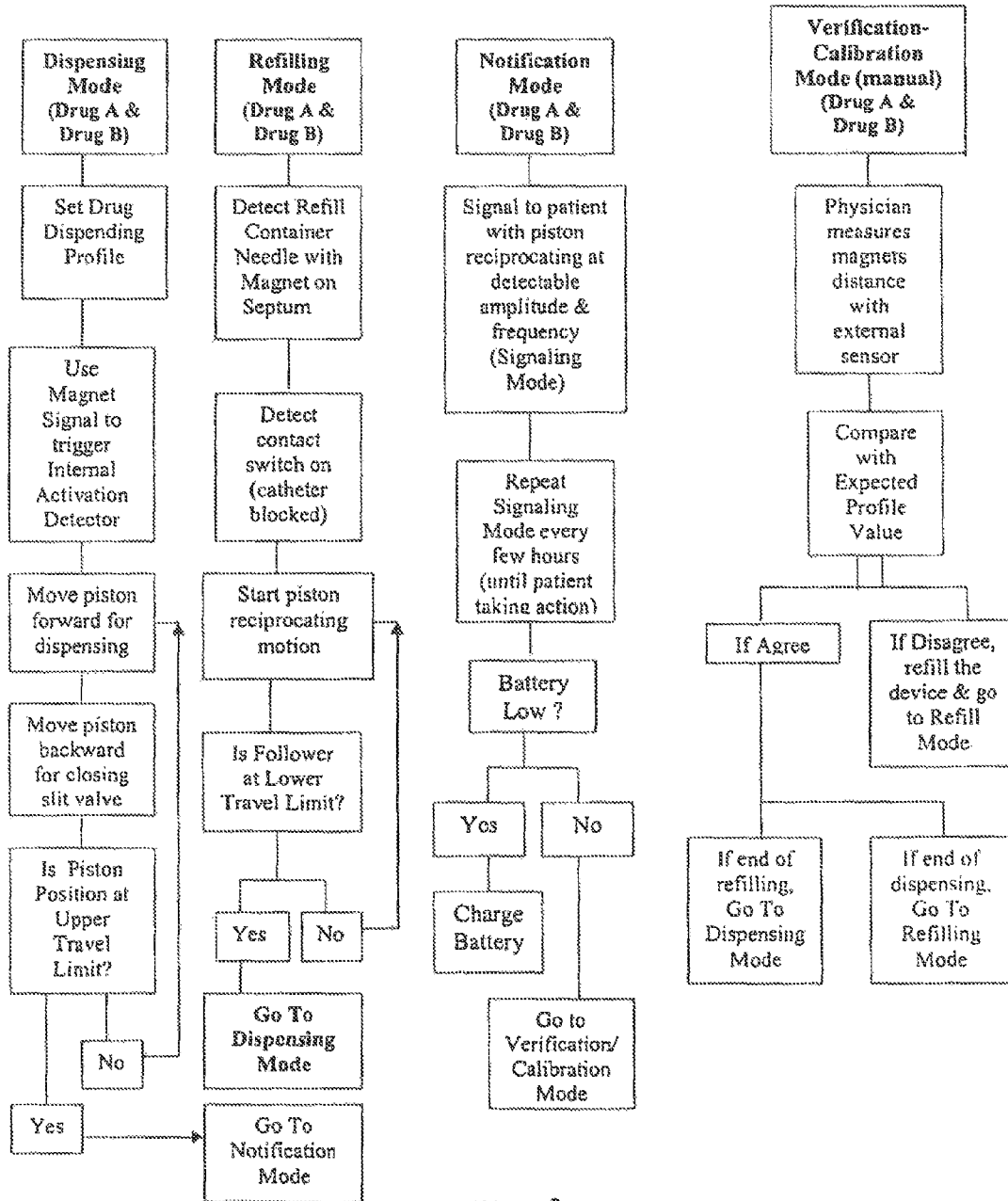
FIG. 19 is a control chart of operation modes of an implantable dual drug delivery device of the present invention

As a summary, FIG. 19 shows the interactions of the operation modes of the software control program of the implantable drug delivery pump of the present invention.

Although the invention has been described with reference to particular embodiments, the description is only an example of the invention's application and should not be taken as a limitation. Various other adaptations and combinations of features of the embodiments disclosed are within the scope of the invention.

We claim:

1. A refill container for refilling an implantable drug delivery device comprising:
   a. a tubular housing with inner wall surface having first opening and second opening, said tubular housing containing a drug fluid,
   b. a needle being attached to the second opening, said needle being in flow communication with the tubular housing,
   c. a disc situated inside said tubular housing in slidable sealing fit with an inner wall surface, said disc not accessible from outside the housing and being only movable following the flow direction toward the needle when the drug fluid is being removed from the housing through the needle, said disc being exposed to ambient pressure through the first opening.

2. The refill container according to claim 1, wherein said tubular housing comprises a valve chamber situated at said second opening end and a reservoir chamber situated at said first opening end, and further comprising
   an orifice plate being positioned separating the valve chamber and the reservoir chamber, said orifice plate having an orifice at the center for passing a drug fluid from the reservoir chamber to the valve chamber, and said valve chamber includes a movable magnet valve having a polarity being situated in said valve chamber such that said magnet valve blocks the opening of the orifice plate when moved in contact with the orifice plate and allows for the flow of the drug fluid from the reservoir chamber to the needle when said magnet valve is moved away from the orifice plate.

3. A refill system of an implantable dual drug delivery device comprising:
   a. a first refill container containing a first drug fluid having a magnet valve with a first polarity,
   b. a second refill container containing a second drug fluid having a magnet valve with a second polarity,
   c. a first drug chamber containing a first drug fluid and having an outlet, a septum and a first piston, said septum being attached with a first magnet with first polarity attracting the magnet valve of the first refill container and repelling the magnet valve of the second refill container,
   d. a second drug chamber containing a second drug fluid and having an outlet, a septum and a second piston, said septum being attached with a second magnet with second polarity attracting the magnet valve of the second refill container, said second polarity being opposite to the first polarity of said first refill container.

* * * * *